(12) United States Patent
Schowengerdt et al.

(10) Patent No.: US 8,076,630 B2
(45) Date of Patent: Dec. 13, 2011

(54) SYSTEM AND METHOD OF EVALUATING AN OBJECT USING ELECTROMAGNETIC ENERGY

(75) Inventors: Brian T. Schowengerdt, Seattle, WA (US); Thomas A. Furness, III, Seattle, WA (US); Ross D. Melville, Issaquah, WA (US); Konrad E. Schroder, Seattle, WA (US); Robert A. Burstein, Seattle, WA (US); Winyu Chinthammit, Mowbray (AU)

(73) Assignee: Visualant, Inc., Seattle, WA (US)

( * ) Notice: Subject to any disclaimer, the term of this patent is extended or adjusted under 35 U.S.C. 154(b) by 466 days.

(21) Appl. No.: 12/375,814

(22) PCT Filed: Jul. 30, 2007

(86) PCT No.: PCT/US2007/017082
§ 371 (c)(1),
(2), (4) Date: Jan. 30, 2009

(87) PCT Pub. No.: WO2008/016590
PCT Pub. Date: Feb. 7, 2008

(65) Prior Publication Data
US 2010/0208240 A1    Aug. 19, 2010

Related U.S. Application Data

(60) Provisional application No. 60/820,938, filed on Jul. 31, 2006.

(51) Int. Cl.
*G06M 7/00* (2006.01)
(52) U.S. Cl. ...................................... 250/221

(58) Field of Classification Search .......... 250/221–243
See application file for complete search history.

(56) References Cited

U.S. PATENT DOCUMENTS

| | | | |
|---|---|---|---|
| 3,499,158 A | 3/1970 | Lavine et al. | 250/217 |
| 3,582,659 A | 6/1971 | Dekker | 250/214 R |
| 3,679,449 A | 7/1972 | Nagot et al. | 117/1 |

(Continued)

FOREIGN PATENT DOCUMENTS

WO    91/05459    5/1991

(Continued)

OTHER PUBLICATIONS

CRi Nuance Multispectral Imaging System, URL=http://www.cri-inc.com/products/nuance.asp, download date Jan. 30, 2007, 2 pages.

(Continued)

*Primary Examiner* — Michael P Stafira
(74) *Attorney, Agent, or Firm* — Seed IP Law Group PLLC

(57) ABSTRACT

A system for evaluating subject objects includes at least one physical source operable to emit electromagnetic energy and driver electronics drivingly coupled to at least one physical source. The driver electronics is configured to drive at least one physical source as a number of logical sources, using an electromagnetic forcing function. The number of logical sources is greater than the number of physical sources. In addition, the system includes a sensor configured to receive an electromagnetic response from at least a portion of an evaluation object illuminated by one or more physical sources operated as logical sources, and convert the electromagnetic response to a test response signal indicative of the electromagnetic response of the evaluation object.

56 Claims, 12 Drawing Sheets

U.S. PATENT DOCUMENTS

| | | | |
|---|---|---|---|
| 3,822,098 A | 7/1974 | Rudder et al. | 356/209 |
| 3,867,039 A | 2/1975 | Nelson | 356/178 |
| 3,922,090 A | 11/1975 | Fain | 356/71 |
| 3,942,185 A | 3/1976 | Lebailly | 357/17 |
| 3,994,590 A | 11/1976 | Di Martini et al. | 356/178 |
| 4,082,188 A | 4/1978 | Grimmell et al. | 209/73 |
| 4,098,940 A | 7/1978 | Groh et al. | 428/218 |
| 4,120,445 A | 10/1978 | Carrier et al. | 229/53 |
| 4,183,989 A | 1/1980 | Tooth | 428/195 |
| 4,241,738 A | 12/1980 | Lübbers et al. | 128/666 |
| 4,277,514 A | 7/1981 | Sugiura et al. | 427/1 |
| 4,325,981 A | 4/1982 | Sugiura et al. | 427/7 |
| 4,652,913 A | 3/1987 | Saitoh et al. | 358/75 |
| 4,678,338 A | 7/1987 | Kitta et al. | 356/402 |
| 4,760,250 A * | 7/1988 | Loeppert | 250/227.23 |
| 4,830,501 A | 5/1989 | Terashita | 356/402 |
| 4,921,278 A | 5/1990 | Shiang et al. | 283/87 |
| 4,952,061 A | 8/1990 | Edgar | 356/407 |
| 5,137,364 A | 8/1992 | McCarthy | 356/402 |
| 5,325,167 A | 6/1994 | Melen | 356/71 |
| 5,377,000 A | 12/1994 | Berends | 356/73 |
| 5,619,326 A | 4/1997 | Takamatsu et al. | |
| 5,844,680 A | 12/1998 | Sperling | |
| 5,933,244 A | 8/1999 | Kiritchenko | 356/402 |
| 5,966,217 A | 10/1999 | Roe et al. | 356/402 |
| 6,020,583 A | 2/2000 | Walowit et al. | 250/226 |
| 6,035,246 A | 3/2000 | Wagner | 700/266 |
| 6,038,024 A | 3/2000 | Berner | 356/326 |
| 6,054,021 A | 4/2000 | Kurrle et al. | 162/140 |
| 6,165,609 A | 12/2000 | Curatolo | 428/343 |
| 6,172,745 B1 | 1/2001 | Voser et al. | 356/71 |
| 6,176,522 B1 | 1/2001 | Jackson | 283/91 |
| 6,255,948 B1 | 7/2001 | Wolpert et al. | 340/572.8 |
| 6,384,918 B1 | 5/2002 | Hubble, III et al. | 356/402 |
| 6,421,553 B1 | 7/2002 | Costa et al. | 600/476 |
| 6,449,045 B1 | 9/2002 | Mestha | 356/402 |
| 6,556,932 B1 | 4/2003 | Mestha et al. | 702/76 |
| 6,560,546 B1 | 5/2003 | Shenk et al. | 702/30 |
| 6,584,435 B2 | 6/2003 | Mestha et al. | 702/196 |
| 6,621,576 B2 | 9/2003 | Tandon et al. | 356/320 |
| 6,633,382 B2 | 10/2003 | Hubble, III et al. | 356/402 |
| 6,639,699 B2 | 10/2003 | Matsuyama | 359/35 |
| 6,690,465 B2 | 2/2004 | Shimizu et al. | 356/326 |
| 6,718,046 B2 | 4/2004 | Reed et al. | 382/100 |
| 6,721,440 B2 | 4/2004 | Reed et al. | 382/100 |
| 6,721,629 B2 | 4/2004 | Wendling et al. | 700/279 |
| 6,724,912 B1 | 4/2004 | Carr et al. | 382/100 |
| 6,731,785 B1 | 5/2004 | Mennie et al. | 382/135 |
| 6,744,909 B1 | 6/2004 | Kostrzewski et al. | 382/115 |
| 6,748,533 B1 | 6/2004 | Wu et al. | 713/176 |
| 6,757,406 B2 | 6/2004 | Rhoads | 382/100 |
| 6,763,124 B2 | 7/2004 | Alattar et al. | 382/100 |
| 6,782,115 B2 | 8/2004 | Decker et al. | 382/100 |
| 6,788,800 B1 | 9/2004 | Carr et al. | 382/100 |
| 6,798,517 B2 | 9/2004 | Wagner et al. | 356/406 |
| 6,804,377 B2 | 10/2004 | Reed et al. | 382/100 |
| 6,888,633 B2 | 5/2005 | Vander Jagt et al. | 356/407 |
| 6,930,773 B2 | 8/2005 | Cronin et al. | 356/300 |
| 6,937,323 B2 | 8/2005 | Worthington et al. | 356/73 |
| 6,968,337 B2 | 11/2005 | Wold | 707/100 |
| 6,992,775 B2 | 1/2006 | Soliz et al. | 356/456 |
| 6,993,535 B2 | 1/2006 | Bolle et al. | 707/104 |
| 6,995,839 B1 | 2/2006 | Shapiro | 356/301 |
| 6,996,478 B2 | 2/2006 | Sunshine et al. | 702/22 |
| 7,001,038 B2 | 2/2006 | Bock et al. | 362/125 |
| 7,003,132 B2 | 2/2006 | Rhoads | 382/100 |
| 7,003,141 B1 | 2/2006 | Lichtermann et al. | 382/124 |
| 7,005,661 B2 | 2/2006 | Yamaguchi et al. | 250/559.16 |
| 7,006,204 B2 | 2/2006 | Coombs et al. | 356/71 |
| 7,008,795 B2 | 3/2006 | Yerazunis et al. | 436/164 |
| 7,012,695 B2 | 3/2006 | Maier et al. | 356/453 |
| 7,016,717 B2 | 3/2006 | Demos et al. | 600/473 |
| 7,018,204 B2 | 3/2006 | Jung et al. | 433/26 |
| 7,023,545 B2 | 4/2006 | Slater | 356/326 |
| 7,026,600 B2 | 4/2006 | Jamieson et al. | 250/221 |
| 7,027,134 B1 | 4/2006 | Garcia-Rubio et al. | 356/39 |
| 7,027,165 B2 | 4/2006 | De Haas et al. | 356/600 |
| 7,027,619 B2 | 4/2006 | Pavlidis et al. | 382/115 |
| 7,031,555 B2 | 4/2006 | Troyanker | 382/305 |
| 7,032,988 B2 | 4/2006 | Darby et al. | 347/14 |
| 7,035,873 B2 | 4/2006 | Weare | 707/104.1 |
| 7,038,766 B2 | 5/2006 | Kerns et al. | 356/71 |
| 7,041,362 B2 | 5/2006 | Barbera-Guillem | 428/206 |
| 7,044,386 B2 | 5/2006 | Berson | 235/491 |
| 7,046,346 B2 | 5/2006 | Premjeyanth et al. | 356/71 |
| 7,046,842 B2 | 5/2006 | Lin et al. | 382/165 |
| 7,049,597 B2 | 5/2006 | Bodkin | 250/353 |
| 7,052,730 B2 | 5/2006 | Patel et al. | 427/7 |
| 7,052,920 B2 | 5/2006 | Ushio et al. | 438/14 |
| 7,058,200 B2 | 6/2006 | Donescu et al. | 382/100 |
| 7,061,652 B2 | 6/2006 | Kurita et al. | 358/3.28 |
| 7,063,260 B2 | 6/2006 | Mossberg et al. | 235/454 |
| 7,170,606 B2 | 1/2007 | Yerazunis | 356/432 |
| 7,171,680 B2 | 1/2007 | Lange | |
| 7,259,853 B2 | 8/2007 | Hubble, III et al. | 356/402 |
| 7,307,752 B1 | 12/2007 | Mestha et al. | 358/1.9 |
| 7,383,261 B2 | 6/2008 | Mestha et al. | 707/7 |
| 7,570,988 B2 * | 8/2009 | Ramanujam et al. | 600/476 |
| 2002/0009213 A1 | 1/2002 | Rowe et al. | |
| 2002/0012447 A1 | 1/2002 | Amidror et al. | 382/100 |
| 2002/0146146 A1 | 10/2002 | Miolla et al. | 382/100 |
| 2002/0176600 A1 | 11/2002 | Rhoads et al. | 382/100 |
| 2003/0031347 A1 | 2/2003 | Wang | |
| 2003/0063772 A1 | 4/2003 | Smith et al. | 382/100 |
| 2003/0095726 A1 | 5/2003 | Kia et al. | 382/313 |
| 2003/0142314 A1 | 7/2003 | Hubble, III et al. | 356/402 |
| 2003/0151611 A1 | 8/2003 | Turpin et al. | 345/589 |
| 2003/0152274 A1 | 8/2003 | McGrew | 382/210 |
| 2003/0156752 A1 | 8/2003 | Turpin et al. | 382/162 |
| 2003/0158617 A1 | 8/2003 | Turpin et al. | 700/97 |
| 2003/0158788 A1 | 8/2003 | Turpin et al. | 705/26 |
| 2003/0174882 A1 | 9/2003 | Turpin et al. | 382/162 |
| 2003/0210805 A1 | 11/2003 | Lofgren et al. | 382/100 |
| 2004/0005086 A1 | 1/2004 | Wolff et al. | 382/118 |
| 2004/0071311 A1 | 4/2004 | Choi et al. | 382/100 |
| 2004/0071366 A1 | 4/2004 | Zhang et al. | 382/284 |
| 2004/0091131 A1 | 5/2004 | Honsinger et al. | 382/100 |
| 2004/0091153 A1 | 5/2004 | Nakano et al. | 382/228 |
| 2004/0101158 A1 | 5/2004 | Butler | 382/100 |
| 2004/0101159 A1 | 5/2004 | Butler | 382/100 |
| 2004/0101168 A1 | 5/2004 | Kostrzewski et al. | 382/115 |
| 2004/0105569 A1 | 6/2004 | Sharma et al. | 382/100 |
| 2004/0119976 A1 * | 6/2004 | Faupel et al. | 356/337 |
| 2006/0059013 A1 | 3/2006 | Lowe | 705/2 |
| 2006/0132790 A1 * | 6/2006 | Gutin | 356/479 |
| 2006/0161788 A1 | 7/2006 | Turpin et al. | |
| 2006/0247532 A1 * | 11/2006 | Ramanujam et al. | 600/476 |
| 2007/0078610 A1 | 4/2007 | Adams et al. | 702/28 |
| 2008/0133389 A1 | 6/2008 | Schowengerdt et al. | |
| 2008/0171925 A1 * | 7/2008 | Xu et al. | 600/316 |
| 2009/0112101 A1 | 4/2009 | Furness, III et al. | |

FOREIGN PATENT DOCUMENTS

| | | |
|---|---|---|
| WO | 03/069884 | 8/2003 |
| WO | 2006050367 A2 | 5/2006 |
| WO | 2008016590 A2 | 2/2008 |

OTHER PUBLICATIONS

CRi Products Components, URL=http://www.cri-inc.com/products/components.asp, download date Jan. 30, 2007, 5 pages.

Furness III et al., "Method, Apparatus, and Article to Facilitate Evaluation of Objects Using Electromagnetic Energy," U.S. Appl. No. 60/834,589, filed Jul. 31, 2006, 135 pages.

Furness III et al., "Method, Apparatus, and Article to Facilitate Evaluation of Objects Using Electromagnetic Energy," U.S. Appl. No. 60/871,639, filed Dec. 22, 2006, 140 pages.

Furness III et al., "Method, Apparatus, and Article to Facilitate Evaluation of Objects Using Electromagnetic Energy," U.S. Appl. No. 60/883,312, filed Jan. 3, 2007, 147 pages.

Furness III et al., "Method, Apparatus, and Article to Facilitate Evaluation of Objects Using Electromagnetic Energy," U.S. Appl. No. 60/890,446, filed Feb. 16, 2007, 155 pages.

Furness III et al., "Method, Apparatus, and Article to Facilitate Evaluation of Objects Using Electromagnetic Energy," U.S. Appl. No. 11/831,717, filed Jul. 31, 2007 156 pages.

Furness III et al., "Method, Apparatus, and Article to Facilitate Evaluation of Objects Using Electromagnetic Energy," Preliminary Amendment filed Jan. 9, 2009 for U.S. Appl. No. 11/831,717, 39 pages.

International Search Report, mailed Jun. 21, 2007, for PCT/US2005/039495, 1 page.

International Search Report, mailed Jul. 23, 2008, for PCT1US2007/017082, 1 page.

Schowengerdt et al., "System and Method of Evaluating an Object Using Electromagnetic Energy," U.S. Appl. No. 60/820,938, filed Jul. 31, 2006, 69 pages.

Schowengerdt et al., "Method, Apparatus, and Article to Facilitate Distributed Evaluation of Objects Using Electromagnetic Energy," U.S. Appl. No. 60/834,662, filed Jul. 31, 2006, 96 pages.

Schowengerdt, B., "Brief Technical Description of the Cyclops Spectral Analysis and Authentication System," Visualant Inc. memorandum, not disclosed prior to Dec. 22, 2006, 2 pages.

Schowengerdt et al., "Method, Apparatus, and Article to Facilitate Distributed Evaluation of Objects Using Electromagnetic Energy," Office Action mailed Jan. 21, 2010 for U.S. Appl. No. 11/831,662, 21 pages.

Schowengerdt et al., "Method, Apparatus, and Article to Facilitate Distributed Evaluation of Objects Using Electromagnetic Energy," Amendment filed Apr. 26, 2010 for U.S. Appl. No. 11/831,662, 41 pages.

Thomas, R., "A Beginners Guide to ICP-MS—Part V: The Ion Focusing System," Spectrospcopy 16(9):38-44, Sep. 2001. (Blank pages appear to be intentional).

Turpin, K., "Full Color Spectrum Object Authentication Methods and Systems," U.S. Appl. No. 60/623,881, filed Nov. 1, 2004, 114 pages.

Turpin et al., "Full Color Spectrum Object Authentication Methods and Systems," U.S. Appl. No. 60/732,163, filed Oct. 31, 2005, 198 pages.

Turpin et al., "Full Color Spectrum Object Authentication Methods and Systems," U.S. Appl. No. 11/264,626, filed Nov. 1, 2005, 46 pages.

Turpin et al., "Full Color Spectrum Object Authentication Methods and Systems," Preliminary Amendment filed Jul. 27, 2006 for U.S. Appl. No. 11/264,626, 3 pages.

Turpin et al., "Full Color Spectrum Object Authentication Methods and Systems," Office Action mailed May 4, 2007 for U.S. Appl. No. 11/264,626, 9 pages.

"Color Technology Beyond the Visible Spectrum Creating Solutions for Product Authentication: Extraordinary Investment Opportunity & 12 Month Roadmap," Visualant Inc., Seattle, Washington, Nov. 17, 2006, 10 pages.

Written Opinion, mailed Jun. 21, 2007, for PCT/US2005/039495, 5 pages.

Written Opinion, mailed Jul. 23, 2008, for PCT/US2007/017082, 3 pages.

Schowengerdt et al., "Method, Apparatus, and Article to Facilitate Distributed Evaluation of Objects Using Electromagnetic Energy," Office Action mailed Jul. 8, 2010 for U.S. Appl. No. 11/831,662, 11 pages.

Vrhel, "An LED based spectrophotometric instrument," *Color Imaging: Device-Independent Color, Color Hardcopy, and Graphic Arts IV, Proceedings of the SPIE 3648*:226-236, Jan. 1999.

* cited by examiner

SYSTEM AND METHOD OF EVALUATING AN OBJECT USING ELECTROMAGNETIC ENERGY

CROSS-REFERENCE TO RELATED APPLICATION

This application claims benefit under 35 U.S.C. §119(e) to U.S. Provisional Patent Application No. 60/820,938, filed Jul. 31, 2006.

BACKGROUND OF THE INVENTION

1. Field of the Invention

This disclosure generally relates to evaluation systems, and more particularly to systems that evaluate characteristics of an object using electromagnetic energy.

2. Description of the Related Art

There are a number of proposed systems that employ spectral analysis of light received from a sample to recognize the sample.

US Patent Application Publication 2006-0161788 A1 describes full color spectrum object authentication methods and systems. In particular, a spectrum measuring device measures a region of respective sampled objects to produce spectral content information that identifies the sampled objects. The spectrum measuring device includes a plurality of individual sensors, which preferably includes specialized narrow band near-infrared and near-ultraviolet sensors, for example photodiodes or photomultipliers. Computers employ spectral analysis software to generate a unique measured pattern, which is then compared with reference patterns stored in a database. The spectral analysis software may be remotely located on a server accessible by the computers. The spectral analysis is preferably performed using XYZ color space modeling, although other color space models may be employed. The region being sampled may be varied to prevent third parties from easily anticipating the location. Samples may be taken from multiple regions to insure accuracy.

U.S. Pat. No. 5,844,680 is directed to a device and process for measuring and analyzing spectral radiation, in particular for measuring and analyzing color characteristics. In particular, a number of radiation sources are provided in combination with a sensor for detecting radiation within a desired wavelength range. The radiation sources have spectral characteristics that are linearly independent from one another, but overlap so that in combination, the radiation sources generate radiation over the entire desired wavelength range. Alternatively, a single radiation source is provided that generates radiation over the entire desired wavelength range, in combination with a plurality of sensors that have spectral sensing characteristics that are linearly independent from one another, but overlap the entire desired wavelength range. A control unit stores a number of calibration functions with linearly independent spectral characteristics.

The patents and other publications directed to the field of object authentication and/or object identification are too numerous to describe. The above described publication and patent are only representative.

BRIEF SUMMARY

It may be useful to determine whether an object being evaluated is identical to a previously evaluated object; in other words determine whether an object being sampled is the exact same object as a reference object. Alternatively, it may be useful to determine whether an object being evaluated is similar to a reference object; in other words determine whether an object being sampled is a facsimile of the reference object. In order to uniquely identify a large number of objects, it may be useful to capture a large number of distinct reference responses from one or more reference objects. This may be difficult to do with fixed illumination. This may also be difficult to do when sensing at a limited number of bands. It may also be useful to separate hardware and/or software functions into separate systems that may be remote to one another. Such may reduce costs and/or permit the use of hardware or software that could not otherwise be financially justified. It may also be useful to apply the object evaluation to specific applications, for example: manufacturing process control, quality assurance, media authentication, biological tissue recognition, identification, verification, authentication, classification, and/or diagnostics.

In one aspect, a system for evaluating subject objects includes at least one physical source operable to emit electromagnetic energy and driver electronics drivingly coupled to the at least one physical source. The driver electronics is configured to drive at least one physical source as a number of logical sources, using an electromagnetic forcing function. At least some of the logical sources have emission spectra different than emission spectra of other logical sources. The number of logical sources is greater than the number of physical sources. In addition, the system includes a sensor configured to receive an electromagnetic response from at least a portion of an evaluation object illuminated by one or more physical sources operated as logical sources, and convert the electromagnetic response to a test response signal indicative of the electromagnetic response of the evaluation object.

In another aspect, a method for evaluating an evaluation object with respect to at least one reference object includes driving at least one physical source of a plurality of physical sources with an electromagnetic forcing function, where each of at least some of the physical sources are driven as a plurality of logical sources. Additionally, the method includes receiving an electromagnetic response from at least a portion of an illuminated region of the evaluation object, converting the electromagnetic response to a test response signal indicative of the response of the illuminated portion of the evaluation object, and comparing the test response signal corresponding to the evaluation object with a reference response signal indicative of a response of at least one reference object to illumination by electromagnetic energy.

BRIEF DESCRIPTION OF THE SEVERAL VIEWS OF THE DRAWING(S)

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Figure 1:
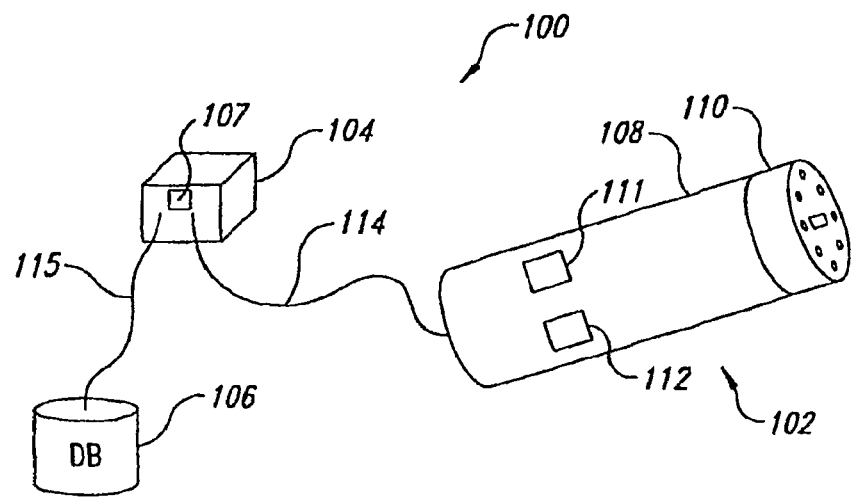
FIG. 1 is a schematic diagram showing an object evaluation system, according to one embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems, networks, servers, microprocessors, memories, buses, and sources of electromagnetic energy have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

The ability to recognize, identify, verify, authenticate and/or classify objects has numerous commercial applications.

It may be useful in some applications to determine whether an object being evaluated is identical to a previously evaluated object; in other words determine whether an object being sampled is the exact same object as a reference object. Alternatively, it may be useful to determine whether an object being evaluated is similar to a reference object; in other words determine whether an object being sampled is a facsimile of the reference object.

For example, it may be useful to determine whether a manufactured object is identical to, or has the same spectral characteristics of a previously evaluated manufactured object. Such may be useful in authenticating goods, and deterring counterfeiting or gray marketing of goods. Such may also be useful in manufacturing process control and/or quality control. Also for example, it may also be useful to determine whether other objects, such as paintings or other works of art are identical to a previously sampled work of art.

For example, it may be useful to determine whether a medium is identical or has the same spectral characteristics as a previously evaluated medium. Such may be useful to determine whether a medium such as a document identical or similar to a previously evaluated document. Such may be useful in recognizing, identifying, verifying, authenticating and/or classifying financial instruments such as currency, checks, bonds, money orders, securities, credit cards, debit cards, and/or gift cards. Such may also be useful in recognizing, identifying, verifying, authenticating and/or classifying identification documents, such as passports, identity cards (e.g., national, state, provincial, military, employer, school, organization), driver's licenses, and/or birth or naturalization certificates. Such may also be useful in recognizing, identifying, verifying, authenticating and/or classifying legal documents such as licenses, permits, assignments, deeds, wills, declarations, oaths, agreements, pleadings, or motions. Such may be useful in recognizing, identifying, verifying, authenticating and/or classifying medical related documents, such as medical records, medical data, medical reports, and/or medical images (e.g., X-Ray, CAT scan, MRI, tomography, etc.). Such may be useful in deterring fraud and/or misuse of documents and other media.

Also for example, it may be useful to determine whether a piece of biological tissue from a subject is the same or similar to a previously evaluated piece of tissue, based on spectral characteristics. Such may be useful in recognizing, identifying, verifying, authenticating, classifying, and/or diagnosing biological tissue or the subject from which the tissue is derived. Bodily tissue may for example include retinal tissue, skin, blood, bone, hair, organs, etc.

It may be particular useful where the above may occur based on the natural conditions or attributes of the object, media, or biological tissue, without the need to apply dedicated indicia such as serial numbers, machine-readable symbols (e.g., barcode symbols, area or matrix code symbols, stack code symbols), and/or radio frequency identification (RFID tags.) Such dedicated data carriers may, in some embodiments, provide additional information regarding the object.

All of the above may, or may not employ additional information about the object to facilitate the process. Additional information may include one or more measurable or observable physical characteristics of the object, media or biological tissue, for example, height, weight, age, hair or eye color, gender, location, type, size, denomination, serial numbers, security features, name, type, serial numbers, date of issue, color, etc. Such additional information may be employed to confirm a match, or to reduce the number of reference responses for comparison with a test response.

The ability to perform such in a network environment may provide a variety of distinct advantages. For example, such may make possible low cost end user test devices, which share or gain remote access to higher cost computing hardware and software. Such may allow the costs of the computing hardware and software to be shared over a variety of end users or financial entities. Such may also allow for "centralization" of relatively higher cost computing hardware and software, perhaps permitting use of high speed super-computers that could not otherwise be financially justified for individual end users or small groups of end users. Such also may allow for "decentralization" of low cost sampling or test device. Such may also allow for light weight and/or low power consuming test devices. Such may additionally or alternatively permit the upgrade of previously distributed test devices. Such may also permit the distribution of work load. Such may also facilitate the backing up of data, and provide for redundancy. Other advantages will be apparent from the teachings herein.

FIG. 1 shows an object evaluation system 100 according to one embodiment of the invention.

The object evaluation system 100 includes an object test device 102, a computer system 104, and a database 106. The object test device 102 includes a control unit 108 and a transducer unit 110. The control unit 108 includes driver electronics 111 and signal processing electronics 112. The computer system 104 may take any of a variety of forms, for example, personal computers, mini-computers, work stations, or main frame computers. The computer system 104 may, for example, take the form of a server computer executing server software. Computer system 104 is well known in the art, and may include a computing device 107, memory, input/output devices, and peripherals. The computing device 107 may be a microprocessor, a central processing unit (CPU), or a virtual device running on the CPU, for example. The memory may include volatile and nonvolatile memory, such as RAM and ROM, and/or include other forms of mass storage devices, including one or more hard disks or RAID drives, CD/ROMs, or other mass storage devices.

In another embodiment, the control unit 108 of the object test device 102 includes the computer system 104. For example, the control unit 108 may include the computing device 107 (e.g., a microprocessor) and memory, as well as user-operable switches and/or a keypad with an electronic display.

The memory may store evaluation software executable by the microprocessor for operating the object test device 102. A user may program the evaluation software to control the object test device 102. In another embodiment, the object test device 102 includes the database 106.

As illustrated in FIG. 1, the object test device 102 is communicatively coupled to the computer system 104 via a first communication cable 114. The first communication cable 114 enables the computer system 104 to send and receive data, control, and power signals to the object test device 102. Additionally, the computer system 104 is communicatively coupled to the database 106 via a second communication cable 115. In another embodiment, the object test device 102, the computer system 104 and the database 106, or any combination thereof, may be configured to support wireless communication of data, control and power signals. Additionally, or alternatively, the object test device 102, computer system 104 and/or database 106 may be communicatively coupled by one or more networks (not shown). The network can take a variety of forms, for example one or more local area networks (LANs), wide area networks (WANs), wireless LANs (WLANs), and/or wireless WANs (WWANs). The network 16a may employ packet switching or any other type of transmission protocol. The network may, for example, take the form of the Internet or Worldwide Web portion of the Internet. The network may take the form of public switched telephone network (PSTN) or any combination of the above, or other networks.

Figure 2:
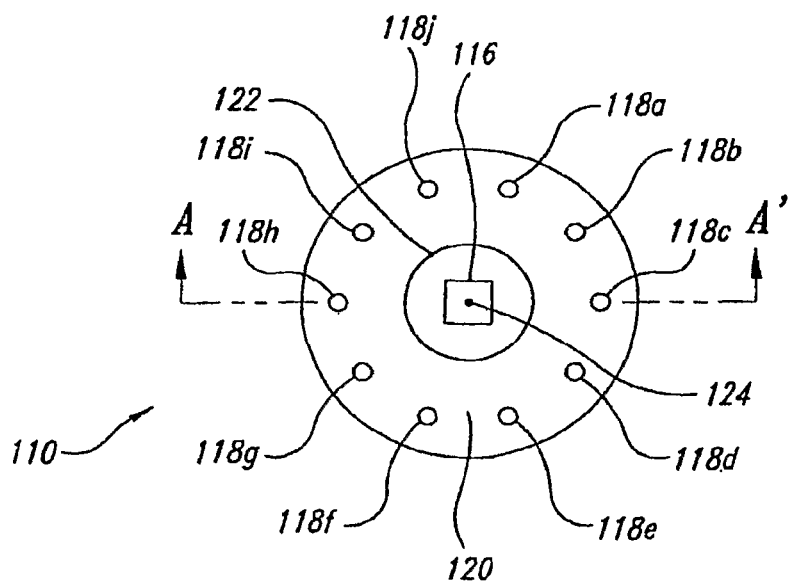
FIG. 2 is an end view showing a transducer unit of the object test device illustrated in FIG. 1, according to one illustrated embodiment.

FIG. 2 is an end view of the transducer unit 110 of the object test device 102 illustrated in FIG. 1.

The transducer unit 110 includes a sensor 116 and N physical sources 118a-118j (collectively 118), where N is a positive integer. For ease of illustration, FIG. 2 shows ten physical sources (i.e., N=10), however any number of physical sources may be employed. The physical sources 118a-118j emit electromagnetic energy. Each source of the physical sources 118a-118j may emit electromagnetic energy in a respective band of the electromagnetic spectrum. If the physical sources 118a-118j are driven at the same power level by the driver electronics 111, then in one embodiment, each physical source of the physical sources 118a-118j has an emission spectrum that is different from the emission spectra of the other physical sources 118a-118j. In another embodiment, at least one physical source of the physical sources 118a-118j has an emission spectrum that is different from the emission spectra of the other physical sources 118a-118j. In one embodiment, the physical sources 118a-118j are light emitting diodes (LEDS). In yet another embodiment, the physical sources 118a-118j are tunable lasers. Alternatively, or additionally, the physical sources 118a-118j may take the form of one or more incandescent sources such as conventional or halogen light bulbs. Alternatively, or additionally, the sources 44 may take the form of one or more organic LEDs (OLEDs, also referred to in the relevant art as "electronic paper"), which may advantageously be formed on a flexible substrate. Alternatively, or additionally, the physical sources 118a-118j may, for example, take the form of one or more sources of microwave, radio wave or X-ray electromagnetic energy.

One, more or all of the physical sources 118a-118j may be operable to emit in part or all of an "optical" portion of the electromagnetic spectrum, including the (human) visible portion, near infrared portion and/or or near ultraviolet portions of the electromagnetic spectrum. Additionally, or alternatively, the physical sources 118a-118j may be operable to emit electromagnetic energy other portions of the electromagnetic spectrum, for example the infrared, ultraviolet and/or microwave portions.

In some embodiments, at least some of the physical sources 118 are operable to emit in or at a different band than other of the physical sources 118. For example, one or more physical sources 118 may emit in a band centered around 450 nm, while one or more of the physical sources 118 may emit in a band centered around 500 nm, while a further source or sources emit in a band centered around 550 nm. In some embodiments, each physical source 118 emits in a band centered around a respective frequency or wavelength, different than each of the other physical sources 118. Using physical sources 118 with different band centers advantageously maximizes the number of distinct samples that may be captured from a fixed number of physical sources 118. This may be particularly advantageous where the test device 102 is relatively small, and has limited space or footprint for the sources 44.

Further, the spectral content for each of the physical sources 118 may vary according to a drive level (e.g., current, voltage, duty cycle), temperature, and other environmental factors. Thus, the emission spectra of each of the sources 118 may have at least one of a different center, bandwidth and/or other more complex differences in spectral content, such as those described above (e.g., width of the band, the skew of the distribution, the kurtosis, etc.) from those of the other sources 118. Such variation may be advantageously actively employed to operate one or more of the physical sources 118 as a plurality of "logical sources," each of the logical sources operable to provide a respective emission spectra from a respective physical source 118. Thus, for example, the center of the band of emission for LEDs may vary according to drive current and/or temperature. One way the spectral content can vary is that the peak wavelength can shift. However, the width of the band, the skew of the distribution, the kurtosis, etc., can also vary. Such variations may be also be advantageously employed to operate the physical sources 118 as a plurality of logical sources. Thus, even if the peak wavelength were to remain constant, the changes in bandwidth, skew, kurtosis, and any other change in the spectrum can provide useful variations in the operation of the object test device 112. Likewise, the center of the band of emission may be varied for tunable lasers. Varying the center of emission bands for one or more physical sources 118 advantageously maximizes the number of samples that may be captured from a fixed number of physical sources 118. Again, this may be particularly advantageous where the test device 102 is relatively small, and has limited space or footprint for the physical sources 118.

A field of emission of one or more physical sources 118 may be movable with respect to a housing. For example, one or more physical sources 118 may be movable mounted with respect to the housing, such as mounted for translation along one or more axes, and/or mounted for rotation or oscillation about one or more axes. Alternatively, or additionally, the test device 102 may include one or more elements operable to deflect or otherwise position the emitted electromagnetic energy. The elements may, for example, include one or more optical elements, for example lens assemblies, mirrors, prisms, diffraction gratings, etc. For example, the optical elements may include an oscillating mirror, rotating polygonal mirror or prism, or MEMS micro-mirror that oscillates about one or more axes. The elements may, for example, include one or more other elements, example permanent magnets or electromagnets such as those associated with cathode ray tubes and/or mass spectrometers. Structures for moving the field of emission and the operation of such are discussed in more detail below.

The sensor 116 can take a variety of forms suitable for sensing or responding to electromagnetic energy. For example, the sensor 116 may take the form of one or more photodiodes (e.g., germanium photodiodes, silicon photodiodes). Alternatively, or additionally, the sensor 116 may take the form of one or more CMOS image sensors. Alternatively, or additionally, the sensor 116 may take the form of one or more charge couple devices (CCDs). Alternatively, or additionally the sensor 116 may take the form of one or more micro-channel plates. Other forms of electromagnetic sensors may be employed, which are suitable to detect the wavelengths expected to be returned in response to the particular illumination and properties of the object being illuminated.

The sensor 116 may be formed as individual elements, one-dimensional array of elements and/or two-dimensional array of elements. For example, the sensor 116 may be formed by one germanium photodiode and one silicon photodiode, each having differing spectral sensitivities. For example, the object test device 112 may employ a number of photodiodes with identical spectral sensitivities, with different colored filters (e.g., gel filters, dichroic filters, thin-film filters, etc) over the photodiodes to change their spectral sensitivity. This may provide a simple, low-cost approach for creating a set of sensors with different spectral sensitivities, particularly since germanium photodiodes are currently significantly more expensive that silicon photodiodes. Alternatively, or additionally, the sensor 116 may take the form of one or more photomultiplier tubes. For example, the sensor 116 may be formed from one CCD array (one-dimensional or two-dimensional) and one or more photodiodes (e.g., germanium photodiodes and/or silicon photodiodes). For example, the sensor 116 may be formed as a one- or two-dimensional array of photodiodes. A two-dimensional array of photodiodes enables very fast capture rate (i.e., camera speed) and may be particular suited to use is assembly lines or high speed sorting operations. For example, the sensor 116 may be formed as a one- or two-dimensional array of photomultipliers. Combinations of the above elements may also be employed.

In some embodiments, the sensor 116 may be a broadband sensor sensitive or responsive over a broad band of wavelengths of electromagnetic energy. In some embodiments, the sensor 116 may be a narrowband sensor sensitive or responsive over a narrow band of wavelengths of electromagnetic energy. In some embodiments, the sensor 116 may take the form of several sensor elements, as least some of the sensor elements sensitive or responsive to one narrow band of wavelengths, while other sensor elements are sensitive or responsive to a different narrow band of wavelengths. This approach may advantageously increase the number of samples that may be acquired using a fixed number of sources. In such embodiments the narrow bands may, or may not, overlap.

In some embodiments, the source 118 may also serve as the sensor 116. For example, an LED may be operated to emit electromagnetic energy at one time, and detect returned electromagnetic energy at another time. For example, the LED may be switched from operating as a source to operating as a detector by reverse biasing the LED. Also for example, an LED may be operated to emit electromagnetic energy at one time, and detect returned electromagnetic energy at the same time, for example by forward biasing the LED.

A field of view of the sensor 116 or one or more elements of the sensor 116 may be movable with respect to the housing. For example, one or more elements of the sensor 116 may be movably mounted with respect to the housing, such as mounted for translation along one or more axes, and/or mounted for rotation or oscillation about one or more axes.

Alternatively, or additionally, the test device 102 may include one or more elements operable to deflect or otherwise position the returned electromagnetic energy. The elements may, for example, include one or more optical elements, for example lens assemblies, mirrors, prisms, diffraction gratings, etc. For example, the optical elements may include an oscillating mirror, rotating polygonal mirror or prism, or MEMS micro-mirror that oscillates about one or more axes. The elements may, for example, include one or more other elements, example permanent magnets or electromagnets such as those associated with cathode ray tubes and/or mass spectrometers.

In some embodiments, the source 118 may also serve as the sensor 116. For example, an LED may be operated to emit electromagnetic energy at one time, and detect returned electromagnetic energy at another time. Also for example, an LED may be operated to emit electromagnetic energy at one time, and detect returned electromagnetic energy at the same time.

The physical sources 118a-118j are mounted on a source end plate 120 and the sensor 116 is mounted on a sensor end plate 122. In another embodiment, the source and sensor end plates 120 and 122, respectively, form a contiguous plate. As illustrated, the physical sources 118a-118j are mounted on the source end plate 120 to form a circle, with the sensor 116 mounted along an axis 124 that is normal to the source end plate 120 and which passes approximately through a center of the circle. The sensor 116 may be located at any position along the axis 124, as will be discussed further below with reference to FIG. 3.

In operation, a user may instruct the computer system 104 via the evaluation software to drive the physical sources 118a-118j in a selected sequence with an electromagnetic forcing function. A physical source emits electromagnetic energy when driven by the electromagnetic forcing function. In one embodiment, the computer system 104 drives the physical sources 118a-118j via the driver electronics 111. The driver electronics 111 may include any combination of switches, transistors and multiplexers, as known by one of skill in the art or later developed, to drive the physical sources 118a-118j in a selected drive pattern.

The electromagnetic forcing function may be a current, a voltage and/or duty cycle. In one embodiment, a forcing function is a variable current that drives one or more of the physical sources 118a-118j in the selected drive pattern (also referred to as a selected sequence). In one embodiment, the computer system 104 drives the physical sources 118a-118j (or any subset of the physical sources 118a-118j) in the selected sequence, in which only one or zero physical sources are being driven at any given instant of time. In another embodiment, the computer system 104 drives two or more physical sources of the physical sources 118a-118j at the same time for an overlapping time period during the selected sequence. The computer system 104 may operate automatically, or may be responsive to user input from a user. Use of the electromagnetic forcing function to drive the physical sources 118a-118j as a number of logical sources is discussed further below with reference to FIG. 4.

Figure 3:
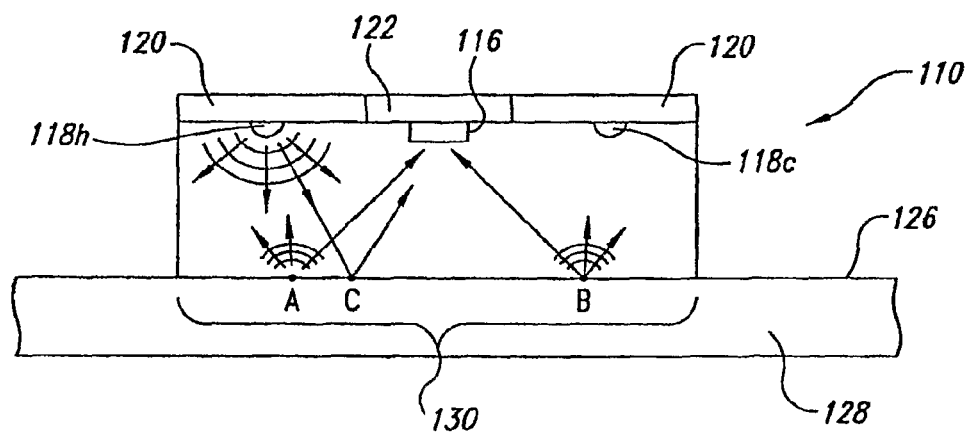
FIG. 3 is a cross-sectional diagram showing an A-A' cross-section of the transducer unit illustrated in FIG. 2, according to one illustrated embodiment.

FIG. 3 shows the transducer unit 110 according to one illustrated embodiment.

The transducer unit 110 may be placed proximate a surface 126 of an evaluation object 128 that is the subject of evaluation. The evaluation object 128 includes objects that reflect, refract, transmit, fluoresce, phosphoresce and/or absorb and re-radiate or otherwise return incident electromagnetic energy. The evaluation object 128 may be in any state of matter, including solid, liquid or gaseous states. Each physical source of the physical sources 118a-118j, when driven, illuminates a portion 130 of the surface 126 of the evaluation object 128. As used herein and in the claims, the terms illuminate, illuminates, illumination, and variations of such terms mean to expose to or reveal by the use of electromagnetic energy or electromagnetic radiation, whether in the visible portion of the electromagnetic spectrum, the optical portion (e.g., visible, near-infrared, near-ultraviolet), or other portions (e.g., far-infrared, far-ultraviolet, microwave, X-ray, etc.).

Typically, the evaluation object 128 reflects, emits, fluoresces or otherwise returns an electromagnetic response to the illumination. The spectral content of the electromagnetic response depends upon the spectrum of the electromagnetic energy incident upon the evaluation object 128 and upon the physical, chemical and electrical properties of the evaluation object 128. Some or all of the electromagnetic response is incident upon the sensor 116.

For example, as illustrated in FIG. 3, driver electronics 111 drives physical source 118h via a user-adjustable electromagnetic forcing function to emit electromagnetic energy. The electromagnetic energy emitted by physical source 118h illuminates a portion 130 of the surface 126 of the evaluation object 128. Based in part upon the contour of the surface 126 and the electrical and chemical properties of the object 128, an electromagnetic response from some or all of the illuminated portion 130 of the surface 126 is received by the sensor 116. For example, an electromagnetic response received by the sensor 116 may be composed of electromagnetic energy emitted from points A and B of the surface 126, comprising reflected and/or re-radiated or otherwise returned light. Other points on the surface 126 may only return electromagnetic energy incident from the physical source 118h. For example, point C only returns electromagnetic energy incident from the physical source 118h. The returned electromagnetic energy from points A, B and C is incident upon the sensor 116. For illustrative ease, only three points A, B and C on the surface 126 are shown to contribute to the electromagnetic response, but many other portions of the surface 126 may also contribute to the response.

Figure 4A:
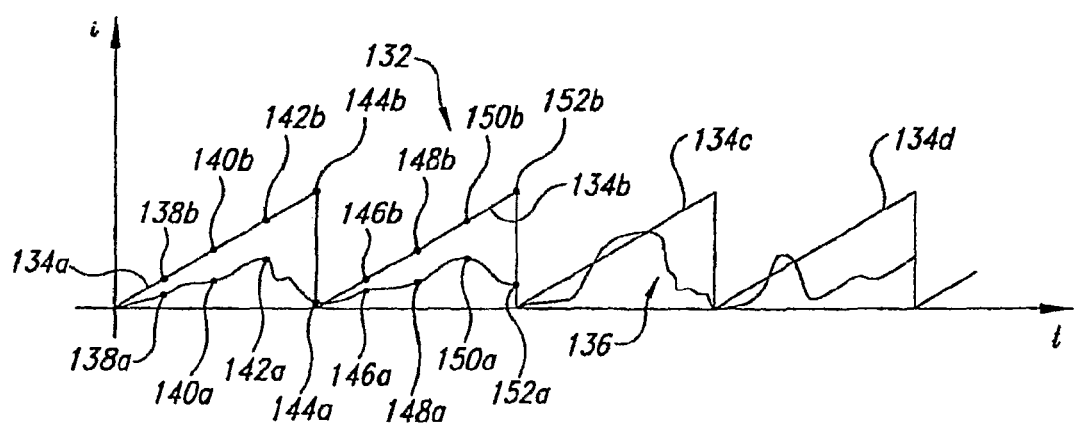
FIGS. 4A-4C are graphs illustrating a portion of an exemplary electromagnetic forcing function that drives physical sources of the transducer unit as a plurality of logical sources, according to one illustrated embodiment.
Figure 4B:
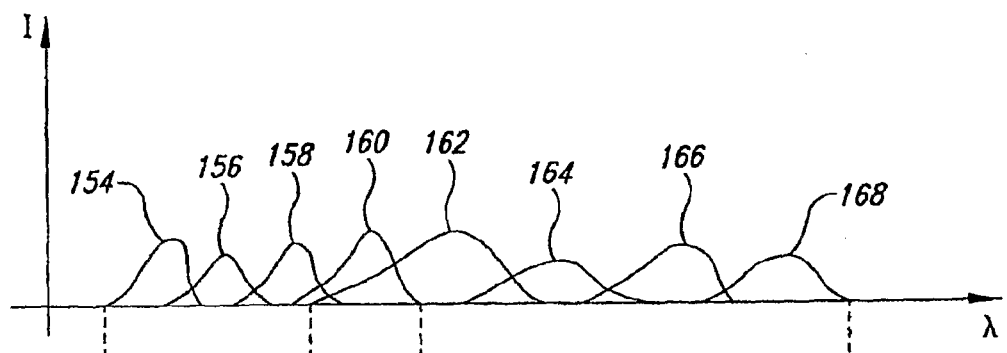
Figure 4C:
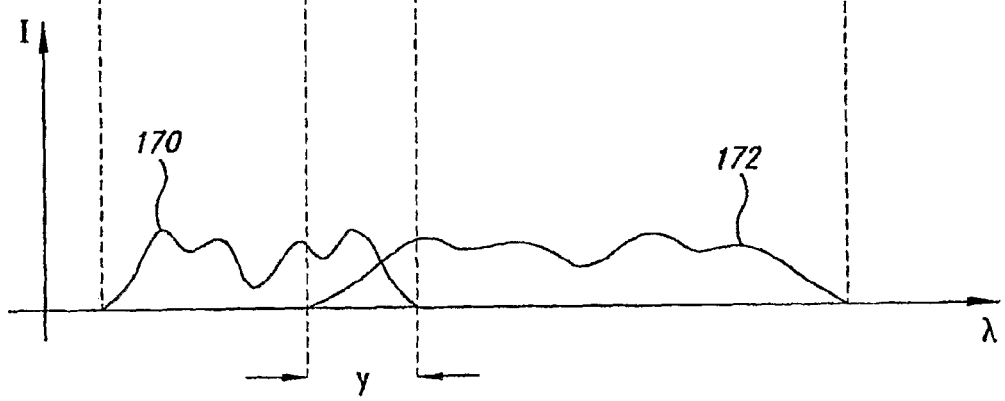

FIGS. 4A-4C illustrate a portion of an electromagnetic forcing function 132 that drives the physical sources 118a-118j as a plurality of logical sources, according to one illustrated embodiment.

In this embodiment, the electromagnetic forcing function 132 is a time varying current with a saw-tooth pattern. The electromagnetic forcing function 132 comprises a plurality of segments 134a-134d (collectively 134). For ease of illustration, FIG. 4A illustrates four segments 134a-134d, however, any suitable number of segments may be employed. In operation, each segment 134 of the electromagnetic forcing function 132 drives one physical source of the physical sources 118a-118j as a number of logical sources. According to one embodiment, the number of logical sources is greater than the number of physical sources 118a-118j. Logical sources will be discussed further below with reference to FIG. 4B.

As an exemplary embodiment, segment 134a drives physical source 118a, segment 134b drives physical source 118b, segment 134c drives physical source 118c and segment 134d drives physical source 118d. A user may instruct the computer system 104 to drive any number of the physical sources 118a-118j in a selected sequence. A user may program the selected sequence via the evaluation software, where the evaluation software may be stored in the memory of the computer system 104. The microprocessor executes the evaluation software programmed by the user and controls the driver electronics 111 in driving the physical sources 118a-118j by the electromagnetic forcing function 132 in the selected sequence.

For example, a user or computer system 104 may select to drive the physical sources 118a-118j in a spatially uniform sequence in which the physical sources 118a-118j are driven in an order in which they are mounted on the source end plate 120 (e.g., {118a, 118b, 118c, . . . , 118i, 118j}), or in a spatially non-uniform sequence, such as (118a, 118d, 118j, 118i, 118e, 118c, 118b, 118g, 118h, 118f). Typically, the selected sequence is repeated until the user or computer system 104 selects a different sequence or the object test device 102 is powered OFF. In another embodiment, the user or computer system 104 may select a subset of the physical sources 118a-118j to be driven in a selected sequence.

As discussed above, the sequence defines an order of activation for the sources 118, and may optionally define a sequence of drive levels for respective ones of the sources 118 within the sequence. In some embodiments, the sequence can be varied periodically. In other embodiments, the sequence may be varied randomly. In further embodiments, the sequence may be varied with each iteration. In still other embodiments, the sequence may be varied based on a time and/or date. Varying the sequence produces an inherent encryption of the signals indicative of the test responses and/or the results. The variation makes it difficult for someone to determine or fake test responses for a given object since the test response varies based on the particular illumination sequence employed. This may be particularly advantageous were security is a concern, for example where identity documents are being authenticated, where financial instruments are being authenticated or where goods are being authenticated to detect forgeries. Thus, the sequence may be varied randomly, periodically, based on time and/or date, or on demand. This inherent variation may be bolstered by more conventional encryption, for example public/private key encryption, for example RSA encryption. Thus, the test response may be encrypted using conventional encryption techniques. Additionally, or alternatively, the sequence may be encrypted using conventional encryption techniques. Additionally, or alternatively, if the sequence is transmitted, it may be transmitted separately from the test results, reducing the likelihood of interception of both. It should be noted that even if both the sequence and resulting test response were intercepted, such information would have limited value since the sequence would or could soon be changed.

Additionally, FIG. 4A illustrates a response signal 136 generated by the sensor 116 upon receiving an electromagnetic response emitted by the evaluation object 128 in response to illumination by the physical sources 118a-118j (or a subset of the physical sources 118a-118j) being driven in the selected sequence by the electromagnetic forcing function 132. In one embodiment, the test response signal 136 is an electrical signal 136. As illustrated, the signal processing electronics 112 (FIG. 1) samples the test response signal 136 at a predetermined sampling rate, as indicated by sampling points 138a, 140a, 142a, . . . , 152a.

According to one embodiment, the electromagnetic forcing function 132 drives each physical source 118 as a plurality of logical sources. That is, a physical source 118 may be considered to be composed of a plurality of logical sources, where each logical source of a given physical source has a respective emission spectrum based upon a value of the electromagnetic forcing function 132 driving the given physical source 118 and upon optical characteristics of the given physical source 118. For example, since the test response signal 136 is sampled four times as a given physical source 118 is being driven, the given physical source 118 operates as four logical sources, where each logical source has a respective emission spectrum or band, different from the emission spectrum or band of the other logical sources for that particular physical source 118. That is, the number of logical sources depends upon the electromagnetic forcing function 132 and the sampling rate of the test response signal 136.

FIG. 4B illustrates four emission spectra 154, 156, 158 and 160 of four logical sources corresponding to the physical source 118a being driven by the forcing function 132 at points 138b, 140b, 142b, and 144b, and four emission spectra 162, 164, 166 and 168 of four logical sources corresponding to the physical source 118b being driven by the forcing function 132 at points 146b, 148b, 150b, and 152b. As illustrated, some emission spectra of the emission spectra 154-168 of the logical sources overlap, however, in an alternate embodiment none of the emission spectra 154-168 overlap with any other of the emission spectra 154-168.

FIG. 4C illustrates a composite emission spectrum 170 for physical source 118a and a composite emission spectrum 172 for physical source 118b. The composite emission spectrum for any given physical source is a summation of the emission spectra of the logical sources for the given physical source. Thus, composite emission spectrum 170 is a summation of the emission spectra 154, 156, 158 and 160 corresponding to the four logical sources generated by driving the physical source 118a at points 138b, 140b, 142b and 146b of the forcing function 132, and composite emission spectrum 172 is a summation of the emission spectra 162, 164, 166 and 168 corresponding to the four logical sources generated by driving the physical source 118b at points 146b, 148b, 150b and 152b of the forcing function 132. As illustrated, the composite emission spectra of the physical sources 118a and 118b overlap one another in a region Y. However, any combination of overlapping and non-overlapping composite emission spectra corresponding to the selected sequence of physical sources being driven may be employed.

Figure 5:
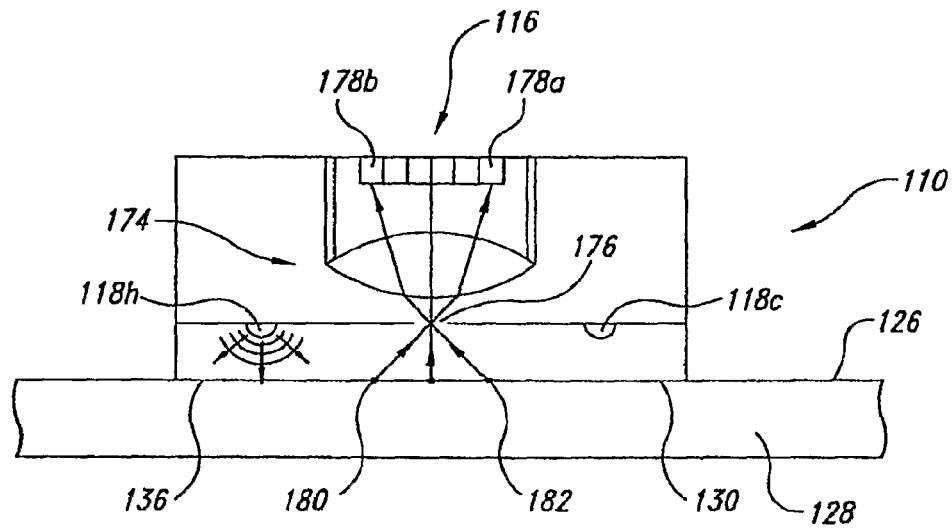
FIG. 5 is a cross-sectional diagram showing an A-A' cross-section of the transducer unit illustrated in FIG. 2, according to another illustrated embodiment.

FIG. 5 shows the transducer unit 110 according to another illustrated embodiment.

The transducer unit 110 includes a focusing device 174 and an aperture 176. However, in other embodiments, the transducer unit 110 may include only the focusing device 174 or only the aperture 176. In this embodiment, the sensor 116 is a detector array having detectors 178. In operation, each physical source of the physical sources 118a-118j driven in a selected sequence emits electromagnetic energy toward the portion 130 of the surface 126 of the evaluation object 128. Each detector of the detectors 178 receives an electromagnetic response returned from a respective portion of the illuminated portion 130 of the evaluation object 128. For example, when physical source 118h is driven, the focusing device 174 focuses an electromagnetic response returned from a respective region 180 of the illuminated portion 130 onto a detector 178a and an electromagnetic response from a respective region 182 of the illuminated portion 130 onto a detector 178b. When physical source 118c is driven, the focusing device 174 focuses a different electromagnetic response from the respective region 180 of the illuminated portion 130 onto the detector 178a.

Each detector (collectively 178) converts an electromagnetic response characteristic of a respective region of the illuminated portion 130 of the evaluation object 128 into a signal characteristic of the respective region. If the sensor 116 includes M detectors 178, then M signals are produced. The signals may be stored in the database 106 (FIG. 1) for further analysis. The focusing device 174 and the aperture 176 allow for a highly reliable evaluation of the evaluation object 128 against known reference objects, since each detector generates a signal that is indicative of an electromagnetic response for a respective sub-portion (i.e., region) of the portion 130. In contrast, the signal generated by the sensor 116 (FIG. 3) is indicative of an electromagnetic response for the portion 130. That is, the signal generated by the sensor 116 is a weighted average of the signals generated by the detectors 178.

Figure 6:
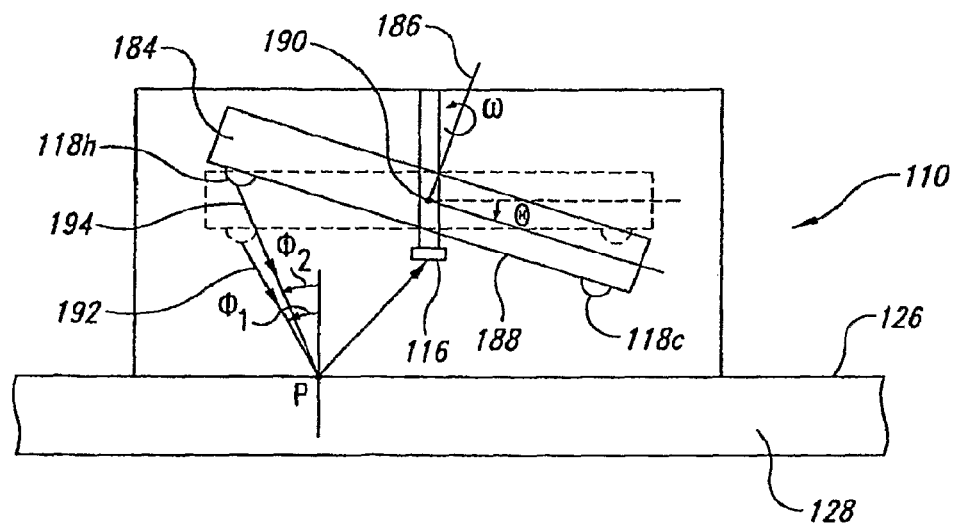
FIG. 6 is a cross-sectional diagram showing an A-A' cross-section of the transducer unit illustrated in FIG. 2, according to a further illustrated embodiment.

FIG. 6 shows the transducer unit 110 according to still another illustrated embodiment.

The transducer unit 110 includes a source mount assembly 184 to which the physical sources 118a-118j are mounted. In one embodiment, the source mount assembly 184 is moveable with respect to the evaluation object 128. In another embodiment, the source mount assembly 184 is moveable with respect to the evaluation object 128 and the sensor 116.

As illustrated in FIG. 6, the source mount assembly 184 is rotatable at a user-defined angular velocity ω about an axis 186, where the axis 186 is perpendicular to a surface 188 of the source mount assembly 184 to which the physical sources 118a-118j are mounted. The source mount assembly 184 may also be pivotable by a user-defined elevation angle θ about an axis 190, where the axis 190 is perpendicular to the axis 186.

When any given physical source of the physical sources 118a-118j emits electromagnetic energy, an angle of incidence of the electromagnetic energy at a given point on the surface 126 of the evaluation object 128 depends upon the elevation angle θ. As illustrated, when the elevation angle θ is zero, $\phi_1$ is the angle of incidence of electromagnetic energy (represented by a ray 192) at a point P on the surface 126. However, when the elevation angle θ is greater than zero, then $\phi_2$ is the angle of incidence of electromagnetic energy (represented by a ray 194) at the point P on the surface 126. Thus, an electromagnetic response may be obtained by driving the physical sources 118a-118j in a selected sequence for a number of different elevation angles θ to illuminate the evaluation object 128.

In an exemplary embodiment, the evaluation object 128 is illuminated by driving the physical sources 118a-118j in the selected sequence for a first elevation angle (e.g., θ=0°), driving the physical sources 118a-118j in the selected sequence for a second elevation angle (e.g., θ=10°), and then driving the physical sources 118a-118j in the selected sequence for a third elevation angle (e.g., θ=20°). The illuminated object 128 emits an electromagnetic response, a portion of which is detected by the sensor 116. The sensor 116 produces a signal indicative of the electromagnetic response. For a given sampling rate, the signal contains three times more data as compared to a signal obtained by driving the physical sources 118a-118j in the selected sequence at only the first elevation angle.

Additionally, the source mount assembly 184 and the physical sources 118a-118j may rotate at a user-defined angular velocity ω about the axis 186. As discussed further below with reference to FIG. 7, driving the physical sources 118a-118j in a selected sequence while rotating the physical sources 118a-118j at an angular velocity ω increases the amount of data contained in the response signal produced by the sensor 116 for a given sampling rate.

Figure 7:
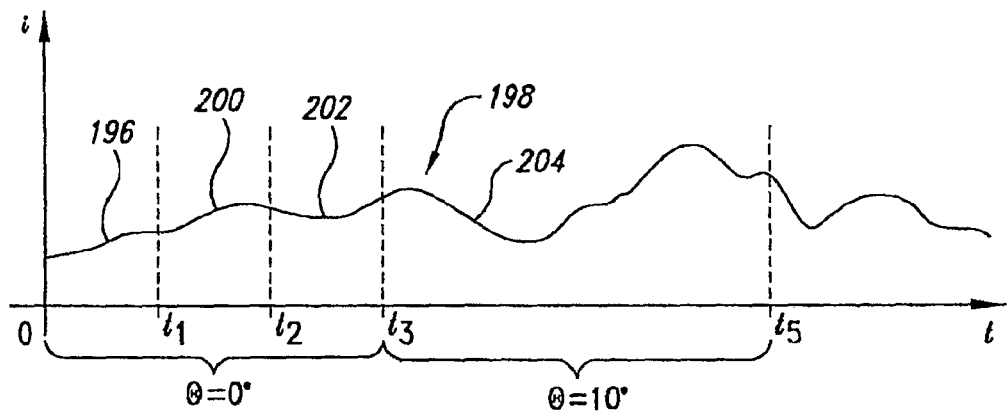
FIG. 7 is a graph illustrating an exemplary test response signal indicative of an electromagnetic response from an evaluation object illuminated by physical sources being driven in a user-selected sequence while being rotated at a given angular velocity for two different elevation angles, according to another illustrated embodiment.
Figure 8A:
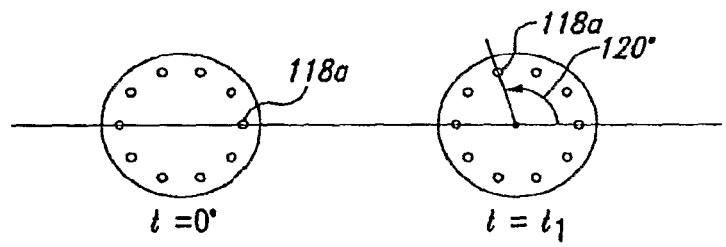
FIGS. 8A-8C are schematic diagrams illustrating the driving of the physical sources through three cycles of a user-selected sequence as a source mount assembly and the physical sources rotate through 360 degrees, according to one illustrated embodiment.
Figure 8B:
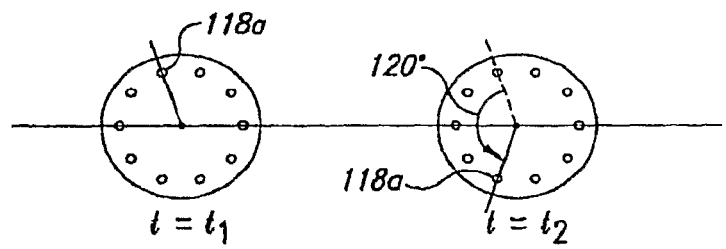
Figure 8C:
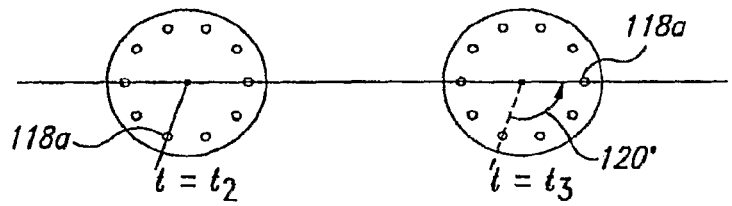

FIG. 7 illustrates a test response signal 198 indicative of an electromagnetic response from the evaluation object 128 (FIG. 6) illuminated by physical sources 118a-118j being driven in a user-selected sequence while being rotated at a given angular velocity ω for two different elevation angles θ, according to one exemplary embodiment. For a first elevation angle θ=0°, the physical sources 118a-118j are driven though one cycle of the user-selected sequence as the source mount assembly 184 and the physical sources 118a-118j rotate through a first 120 degrees, as illustrated in FIG. 8A. In response to detection of an electromagnetic response returned by the evaluation object 128, the sensor 116 generates a first portion 196 of the test response signal 198. Then the physical sources 118a-118j are driven though another cycle of the user-selected sequence as the source mount assembly and the physical sources 118a-118j rotate through a second 120 degrees, as illustrated in FIG. 8B. In response to detection of the electromagnetic response returned by the evaluation object 128, the sensor 116 generates a second portion 200 of the test response signal 198. The physical sources 118a-118j are then driven though another cycle of the user-selected sequence as the source mount assembly and the physical sources 118a-118j rotate through a third 120 degrees, as illustrated in FIG. 8C. In response to detection of the electromagnetic response returned by the evaluation object 128, the sensor 116 generates a third portion 202 of the test response signal 198.

For a second elevation angle θ=10°, for example, the physical sources 118a-118j are driven though three more cycles of the user-selected sequence as the source mount assembly 184 and the physical sources 118a-118j rotate through another 360°, and thereby generating a fourth portion 204 of the test response signal 198. For a given sampling rate, the test response signal 198 comprising portions 196, 200, 202 and 204 contains six times more data as compared to a test response signal obtained by driving the physical sources 118a-118j in the selected sequence at only one elevation angle θ with zero angular velocity ω.

Figure 9A:
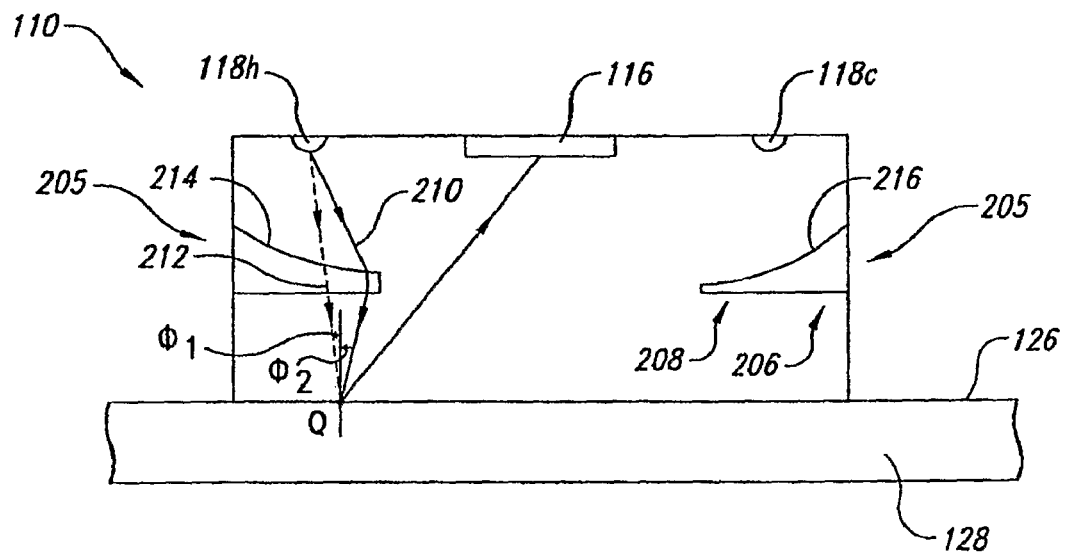
FIG. 9A is a cross-sectional diagram showing an A-A' cross-section of the transducer unit illustrated in FIG. 2, according to one illustrated embodiment.

FIG. 9A shows the transducer unit 110 according to a further illustrated embodiment.

The transducer unit 110 includes an electromagnetic energy directional assembly 205 having a base portion 206 and a circumferential portion 208. The directional assembly 204 modifies an angle of incidence of electromagnetic energy emitted by a physical source incident at a given point on the surface 126. In one embodiment, the directional assembly 204 is a concave lens.

As an exemplary embodiment, electromagnetic energy emitted by physical source 118h and refracted by the directional assembly 205 (and represented by ray 210) is incident at a point Q on the surface 126 of the evaluation object 128 at an angle $\phi_2$. However, with the directional assembly 205 removed from the transducer unit 110, electromagnetic energy (represented by ray 212) emitted by physical source 118h is incident at the point Q on the surface 126 of the evaluation object 128 at an angle $\phi_1$. Thus, the directional assembly 205 modifies the angle of incidence from $\phi_1$ to $\phi_2$, thereby modifying the electromagnetic response of the point Q to the incident electromagnetic energy and subsequently modifying the signal produced by the sensor 116 in response to receiving the electromagnetic response returned by the evaluation object 128.

Figure 9B:
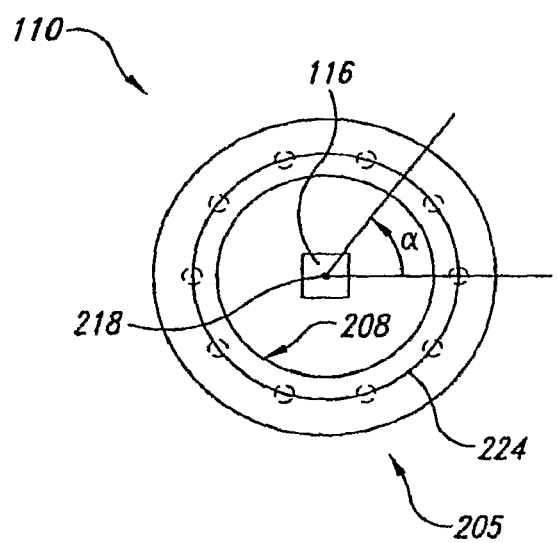
FIG. 9B is an end view of the transducer unit illustrated in FIG. 9A.

FIG. 9B shows the transducer unit 110 according to still a further illustrated embodiment.

The circumferential portion 208 of the directional assembly 205 has an index of refraction that depends upon an angular position a. In one embodiment, a surface of the directional assembly 205 varies as a function of the angular position a to vary an effective index of refraction of the directional assembly 205 as a function of the angular position a. For example, a surface 214 (FIG. 9A) has a different shape (e.g., a different concavity) than a surface 216. In another embodiment, an index of refraction of the concave lens 205 depends upon a lens composition that varies as a function of the angular position α. In another embodiment, the directional assembly 205 rotates about an axis 218 (FIG. 9B) with a user-selected angular velocity.

Figure 9C:
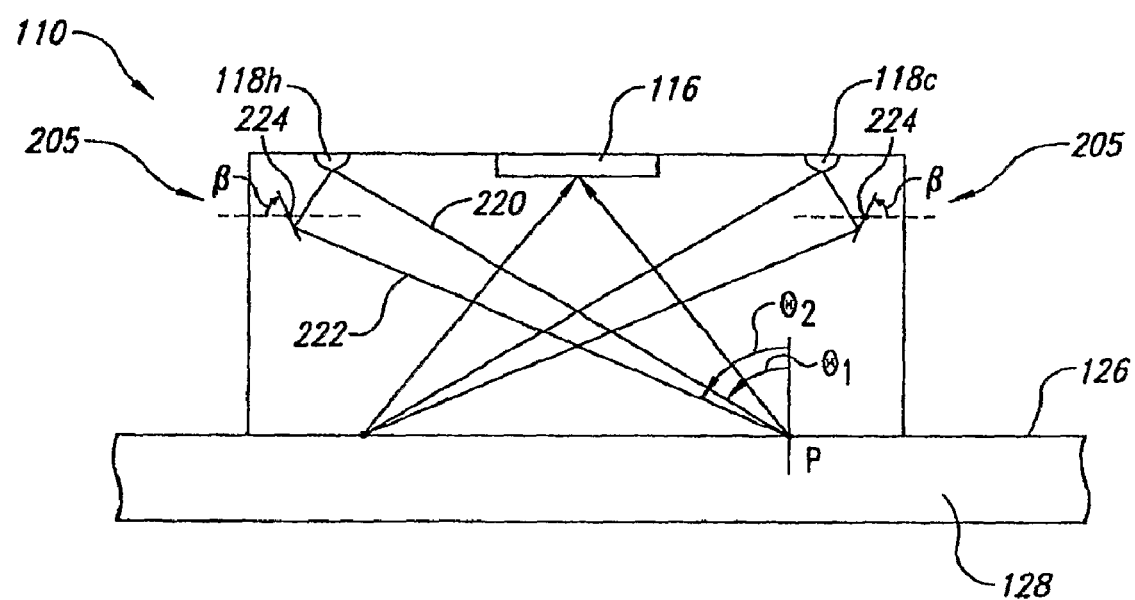
FIG. 9C is a cross-sectional diagram showing an A-A' cross-section of the transducer unit illustrated in FIG. 2, according to another illustrated embodiment.

FIG. 9C shows the transducer unit 110 according to yet a further illustrated embodiment.

As illustrated, the electromagnetic energy directional assembly 205 is a rotatable mirror. When physical source 118h is driven, electromagnetic energy (represented by ray 220) is directly transmitted at an angle of incidence $\phi_1$ to a point P on the surface 126 of the evaluation object 128, and electromagnetic energy (represented by ray 222) is transmitted at an angle of incidence $\phi_2$ to the point P via reflection by the rotatable mirror 205.

In one embodiment, the mirror 205 is rotatable about a circumferential axis 224 (FIGS. 9B and 9C). For example, in operation, the physical sources 118-118j are driven through one or more cycles of a selected sequence while a mirror elevation angle $\beta$ is incrementally modified about the circumferential axis 224.

Figure 10:
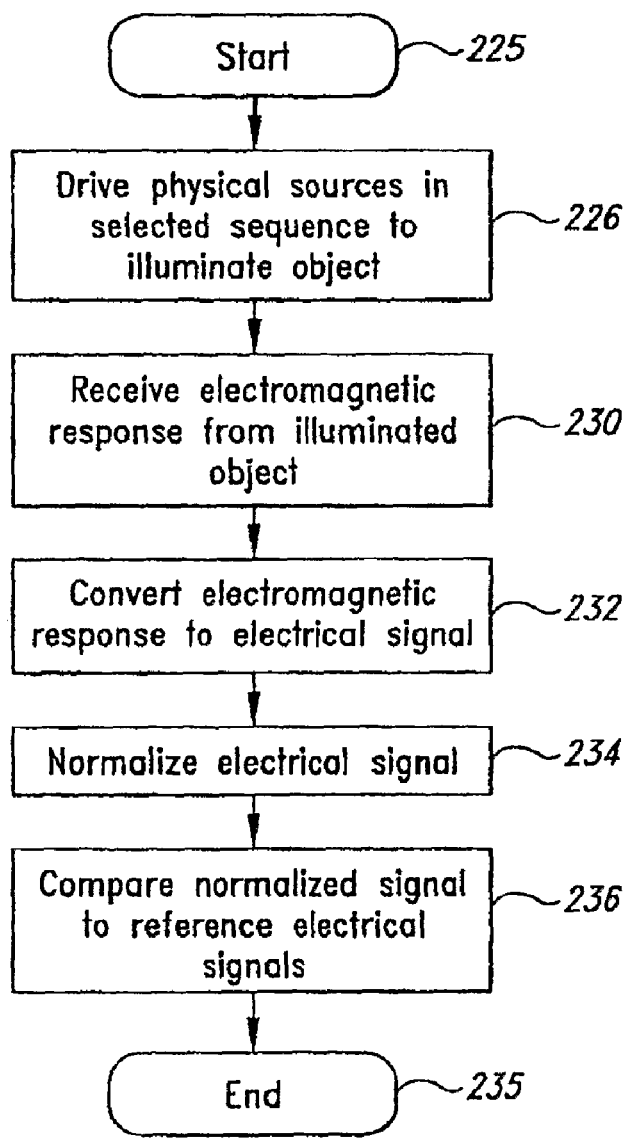
FIG. 10 is a flow chart showing a method of evaluating an object by the object test device illustrated in FIG. 1, according to one illustrated embodiment.

FIG. 10 is a flow chart showing a method of evaluating an evaluation object 128 by the object test device 102, according to one embodiment.

The method starts at 225. At 226, a user drives the physical sources 118a-118j in a selected sequence with an electromagnetic forcing function 132 to emit electromagnetic energy toward the evaluation object 128. Any number of the physical sources 118a-118j may be driven in any order which may include driving any number of the physical sources 118a-118j for overlapping periods of time. In one embodiment, the electromagnetic forcing function 132 is configured to drive a physical source 118 as a number of logical sources, where at least some of the logical sources have different emission spectra than other of the logical sources.

In one embodiment, the object test device 102 includes a computing device 107, memory and evaluation software (not shown). The user may program the object test device 102 to drive any number of the physical sources 118a-118j in the selected sequence. The selected sequence may be stored in the memory. The microprocessor may later retrieve the selected sequence from the memory when evaluating a test signal indicative of an evaluation object against reference signals indicative of reference objects. In one embodiment, the reference signals are electrical reference response signals.

In another embodiment, the computer system 104 (having a microprocessor and memory) automatically selects a sequence to drive any number of the physical sources 118a-118j. The selection may be based, for example, on a time of day, day of the week, or a random number generated by random number generator (RNG) software stored in memory and executed by the microprocessor. RNG software is commercially available.

At 230, the sensor 116 receives an electromagnetic response returned from the evaluation object 128. A spectral content of the electromagnetic response is based upon the optical properties of the evaluation object 128, the emission spectra of the logical sources and the electromagnetic forcing function 132. The shape (in time) of the electromagnetic response depends additionally upon the sequence selected for driving the physical sources 118a-118j. At 232, the sensor 116 converts the electromagnetic response to a signal. The signal is based upon the spectral sensitivity and the gain of the sensor 116. The signal is indicative of the electromagnetic response of the evaluation object 128 to illumination by the selected sequence of physical sources 118a-118j driven as a number of logical sources.

At 234, the microprocessor (not shown) normalizes the signal using normalization factors and the computer-generated or user-selected physical source sequence. When the physical sources 118a-118j are LEDs, the spectral distribution and intensity of the spectral components of the logical sources for each physical source may depend upon ambient operating temperature and variations in processing steps and material composition in the manufacture of the physical sources 118a-118j. Thus, the database 106 may store normalization or calibration factors. The calibration may be based on a variety of factors or parameters. For example, the calibration may be based on a batch number in the manufacture of the physical sources 118a-118j, for example, and/or upon the ambient operating temperature of the physical sources 118a-118j when being driven by the electromagnetic forcing function 132. As is well known to one of skill in the art, the optical characteristics of electromagnetic energy emitted by LEDs may depend upon other factors as well. All normalization or calibration factors that normalize the optical characteristics of electromagnetic energy emitted by light emitting diodes or other types of physical sources or the sensor 116 may be employed in various embodiments. For example, variations between different manufactures, different batches of physical sources 118 by the same manufacturer, or even between individual physical sources 118 in the same manufacturing batch may be accommodated.

At 236, the microprocessor, using the selected physical source driving sequence, compares the normalized test signal to reference signals stored in the database 106. The reference signals are indicative of electromagnetic responses to illumination of reference objects with electromagnetic energy. By comparing the normalized test signal to the reference signals, the microprocessor evaluates the evaluation object 128 against the reference objects. In one embodiment, the microprocessor may rank the likelihood of the evaluation object 128 being identical to, or a copy of, one or more of the reference objects. The microprocessor may produce an indication of a confidence level in the match. The confidence level may be represented in a variety of ways, for example as a percentage of discrepancies detected or how many standard deviations the match is from being an identical match. Alternatively, the confidence level may indicate the number of times a match with a threshold was found. For example, if a match was found in response to more than one sequence, at more than one location, and/or at more than one viewpoint or angle.

In another embodiment, the microprocessor samples the normalized test signal at a predefined sampling rate and compares the sampled test signal to the reference signals. In yet embodiment, the microprocessor evaluates the evaluation object 128 against the reference objects by computing a root-mean-squared (RMS) value for each sampled test signal compared to a reference signal. The method terminates at 235.

Figure 11:
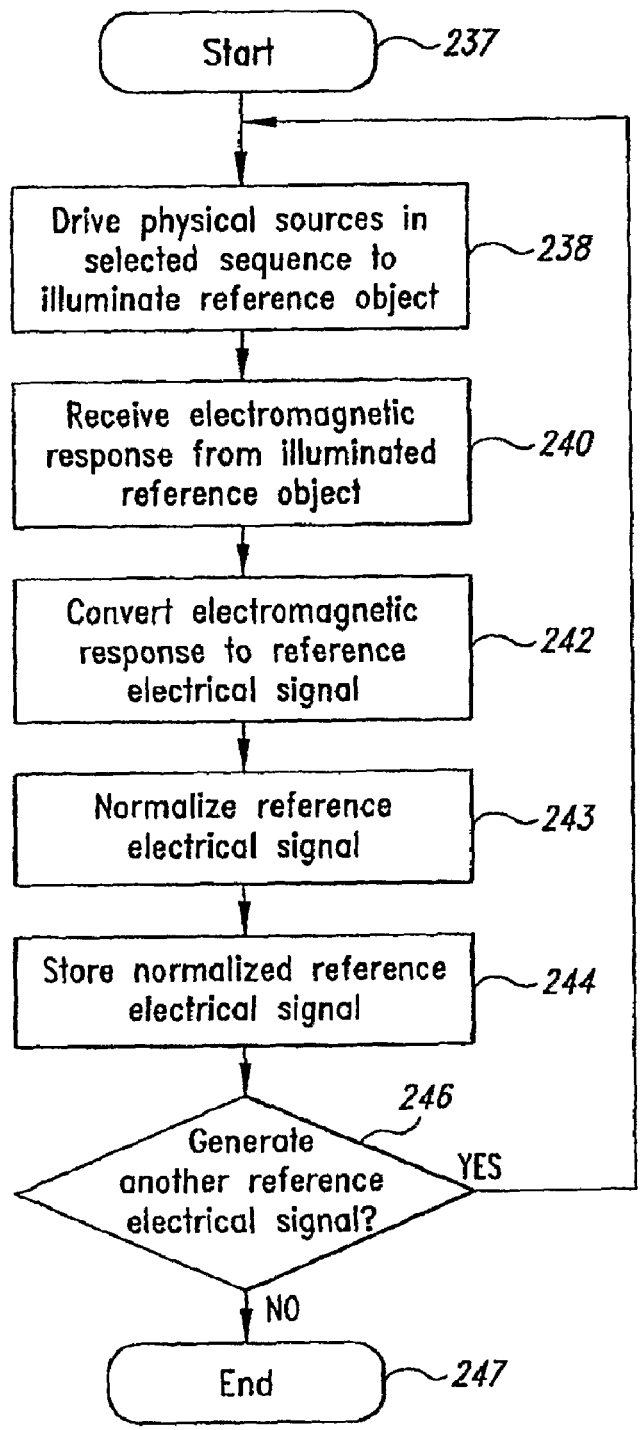
FIG. 11 is a flow chart showing a method of generating reference response signals indicative of electromagnetic responses of reference objects to illumination by electromagnetic energy, according to one illustrated embodiment.

FIG. 11 is a flow chart showing a method of generating reference response signals indicative of electromagnetic responses of reference objects to illumination by electromagnetic energy, according to one illustrated embodiment.

The method starts at 237. At 238, a microprocessor (not shown) of computer system 104 drives the physical sources 118a-118j in a user-selected or automated computer-selected sequence with an electromagnetic forcing function 132 to illuminate the reference object 128 with electromagnetic energy. The physical sources 118a-118j are driven as a plurality of logical sources. The selected sequence includes driving any number of the physical sources 118a-118j in any order. The microprocessor drives the physical sources 118a-118j such that the electromagnetic response from the illuminated reference object 128 includes a plurality of segments, where each segment is an response corresponding to illumination of the reference object 128 by a given physical source of the physical sources 118a-118j.

At 240, the sensor 116 receives the electromagnetic response returned by the reference object 128. The spectral content of the electromagnetic response is based upon the optical properties of the reference object 128, the emission spectra of the plurality of logical sources and the electromagnetic forcing function 132. At 242, the sensor 116 converts the electromagnetic response to a reference signal. The reference signal is additionally based upon the spectral sensitivity and the gain of the sensor 116. The reference signal is indicative of the electromagnetic response returned by the reference object in response to the sequence of illumination.

At 243, the microprocessor normalizes the reference response signal using normalization factors and the computer-selected or user-selected source driving sequence. At 244, the microprocessor stores the reference signal and the associated source driving sequence in the database 106. The microprocessor may also store identifying characteristics or other information about the reference object 128.

At 246, the user or computer system 104 decides whether to generate another reference signal by illuminating and evaluating another reference object with the object test device 102. If, at 246, the user decides to generate another reference signal, the method continues at 238. Otherwise, the method ends at 247.

Figure 12:
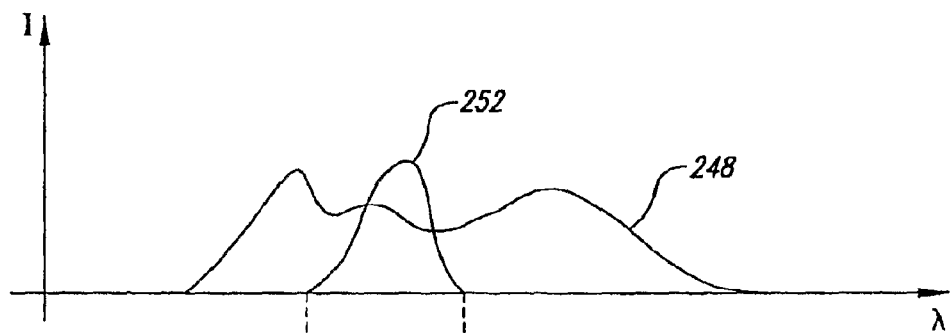
FIGS. 12-14 are schematic diagrams showing construction of an exemplary reference response signal, according to one illustrated embodiment.
Figure 13:
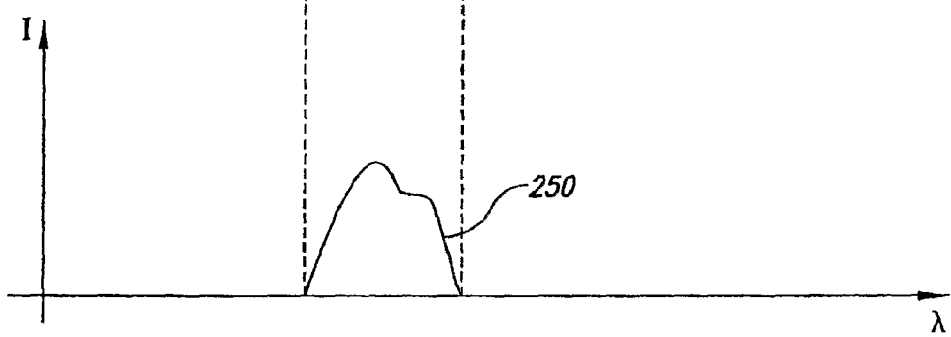
Figure 14:
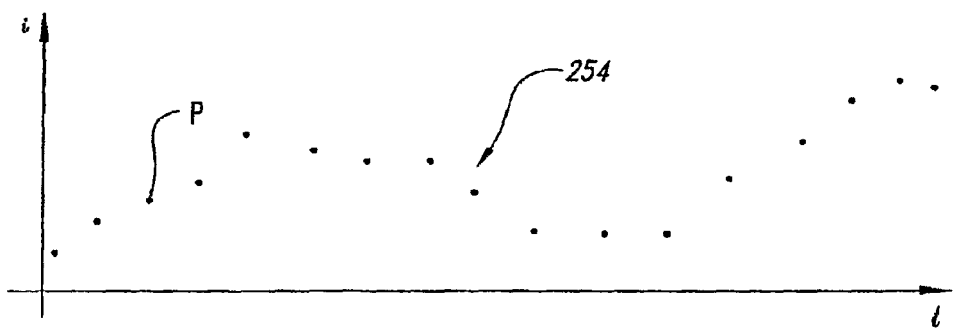

FIGS. 12-14 illustrate construction of a reference response signal, according to another illustrated embodiment.

In order to construct a reference response signal indicative of a response to illumination of a reference object by the physical sources 118a-118j being driven as a plurality of logical sources by an electromagnetic forcing function, a broadband spectral response 248 of the reference object (also referred to as a white light spectral response) is stored in the memory (not shown) of the computer system 104 or in the database 106. In one embodiment, the broadband spectral response 248 of a reference object of a given material composition or with a particular surface color coating is obtained from a third party vendor or from the manufacturer of the reference object. For example, a paint manufacturer may know the spectral content of an electromagnetic response produced by illuminating a particular paint with either a white light source or a plurality of sources having overlapping emission spectra that collectively cover a large portion of the electromagnetic spectrum from the far UV to the far IR, for example.

The microprocessor (not shown) of the computer system 104 computes a spectral response 250 corresponding to illumination of the reference object with a logical source having an emission spectrum 252. In one embodiment, the spectral response 250 is the product of the emission spectrum 252 of the logical source with the broadband spectral response 248. However, one of skill in the art will appreciate other methods for computing the spectral response 250 of the reference object to illumination with a logical source having the emission spectrum 252.

The microprocessor computes a point P of a signal 254 based upon a sensitivity and gain of the sensor 116 and the spectral response 250. Methods for computing data points of an electrical response of a detector to input signals having known spectral distributions are well known in the art.

Figure 15:
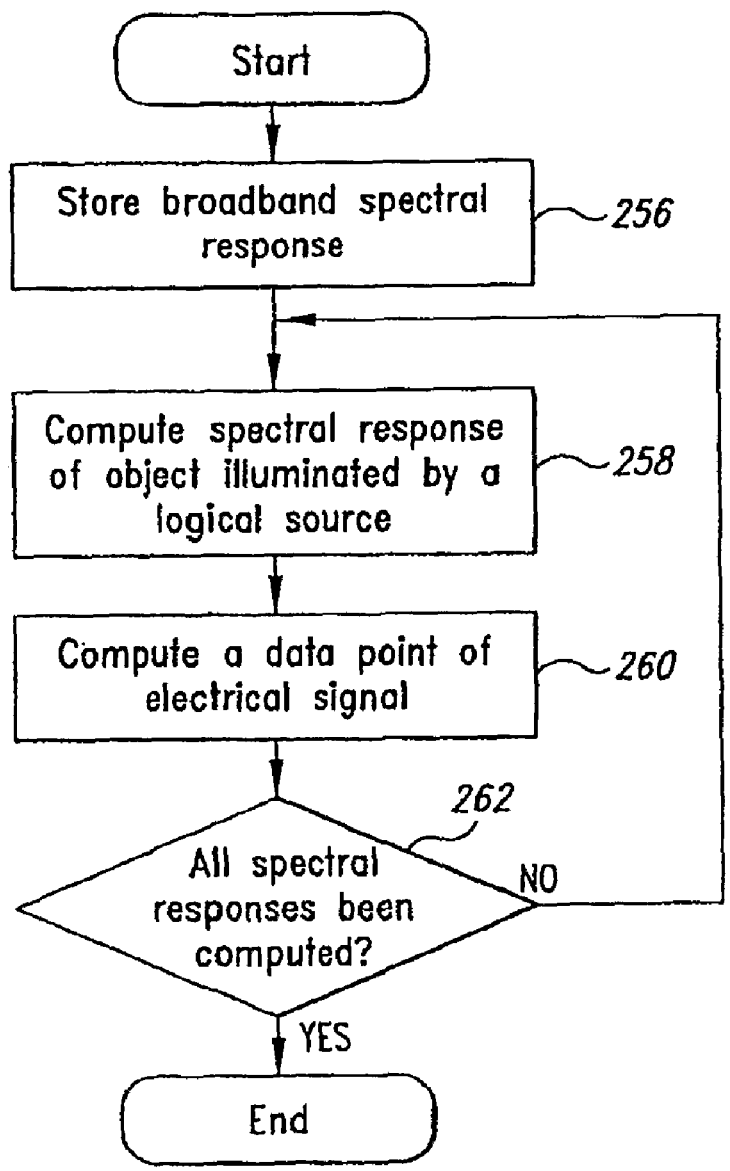
FIG. 15 is a flow chart showing a method of constructing reference response signals indicative of an electromagnetic response of reference objects to illumination by electromagnetic energy supplied by physical sources being driven as N logical sources, according to another illustrated embodiment.

FIG. 15 is a flow chart showing a method of constructing a reference signal indicative of an electromagnetic response of a reference object to illumination by electromagnetic energy supplied by physical sources 118a-118j being driven as N logical sources, according to another illustrated embodiment.

At 256, the broadband spectral response 248 of the reference object 128 is stored in the memory (not shown) of the computer system 104 or in the database 106.

At 258, the microprocessor (not shown) of the computer system 104 computes the spectral response 250 corresponding to illumination of the reference object 128 by a logical source having an emission spectrum 252. At 260, the microprocessor computes the point P of a response signal 254 based upon a sensitivity and gain of the sensor 116 and the spectral response 250.

At 262, the microprocessor determines whether spectral responses corresponding to illumination of the reference object 128 by N logical sources have been computed. If not, then the method continues at 258, and at 260 the microprocessor computes another point of the signal 254. Acts 258-260 are repeated until N points of the signal 254 have been determined, where each point represents illumination of the reference object by one logical source of the N logical sources.

In another embodiment, the computer system 104 is configured to construct a reflectance function (also referred to as a reflectance or a reflectivity) of the evaluation object 128 based upon response signals (e.g., electrical signals) received from the sensor 116. The test response signals are indicative of an electromagnetic response of the evaluation object 128 to illumination by a selected sequence of physical sources 118 driven as a plurality of logical sources. In the discussion that follows, the sensor 116 comprises one or more detector elements (e.g., photomultipliers).

A $j^{th}$ logical source of the plurality of logical sources is defined to have a spectral emittance function $l_j(f)$. That is, the $j^{th}$ logical source produces electromagnetic energy of intensity $p=l_j(f)$ at any given frequency f. Additionally, a $k^{th}$ detector element of the sensor 116 is characterized by a detector response function $m_k(f)$ that gives the $k^{th}$ element's sensitivity to electromagnetic energy of a given frequency f. Furthermore, let $c_{jk}(f)=l_j(f)m_k(f)$, where $c_{jk}(f)$ is a composite function of the $j_{th}$ logical source and the $k_{th}$ detector element. Defining r(f) to be the reflectance of the evaluation object 128, the projection of the reflectance function r(f) on the $c_{jk}(f)$ composite function is the inner product of the reflectance function r(f) with the composite function $c_{jk}(f)$ (i.e., $<c_{jk}(f),r(f)>=\int l_j(f) m_k(f)r(f)df$). The inner product $<c_{jk}(f),r(f)>$ is the test response signal produced by the kth detector element when the $k^{th}$ detector element receives an electromagnetic response from the evaluation object 128 being illuminated by the $j^{th}$ logical source. Assuming that the set of functions $C=\{c_{jk}(f)\}$ are linearly independent (i.e., $<c_{jk},c_{mn}>=0$ when (j≠m, k≠n), (j=m, k≠n) or (j≠m, k=n)), then the reflectance function r(f) $=\Sigma_{j,k}\{<c_{jk},r>/\|c_{jk}\|\}$, where $\|c_{jk}\|=\sqrt{(<c_{jk},c_{jk}>)}=\sqrt{\int c_{jk}(f)c_{jk}(f)df}$).

Linear independent composite functions $c_{jk}(f)$ may be constructed in several ways. In one embodiment, the plurality of physical sources 118 and the forcing function 132 are selected such that plurality of logical sources are linearly independent (i.e., $<l_h(f),l_n(f)>=0$ for h≠n, where $l_h(f)$ is the spectral emittance function of the $h^{th}$ logical source) and the detectors of the sensor 116 are linearly independent ($<m_h(f),m_n(f)>=0$, for h≠n). In this embodiment, the composite functions $c_{jk}$, built from products of linearly independent logical sources and linearly independent detector elements are also linearly independent.

When the logical sources and/or detector elements are not linearly independent, a set of linearly independent composite functions $c_{jk}$ may still be formed, according to another embodiment. By way of example, suppose that the transducer unit 110 includes one or two physical sources 118 being driven as three logical sources having spectral emittance functions $l_1(f), l_2(f)$ and $l_3(f)$. Also suppose that the sensor 116 includes two detector elements characterized by detector response functions $m_1(f)$ and $m_2(f)$. Additionally, assume that a frequency domain F comprised of four disjoint frequency sub-domains $F_1$, $F_2$, $F_3$ and $F_4$ exist in which the logical sources and the detector elements are configured to operate. That is, assume that $l_1(f)=1$ when f is a member of $F_1 \cup F_2$ and $l_1(f)=0$ otherwise, $l_2(f)=1$ when f is a member of $F_3 \cup F_4$ and $l_2(f)=0$ otherwise, $l_3(f)=1$, $m_1(f)=0$ when f is a member of $F_4$ and $m_1(f)=1$ otherwise, and $m_2(f)=0$ when f is a member of $F_1$ and $m_2(f)=1$ otherwise.

Thus, one orthogonal basis set of composite functions $c_{jk}$ comprises $C=\{c_{jk}\}=\{l_2 m_1, l_3 m_1, l_1 m_2, l_3\ m_2\}$. That is, no element of the basis set may be written as a linearly combination of the remaining elements of the basis set. Other orthogonal basis sets may be determined. For example, $C'=\{l_1 m_1, l_3 m_1, l_2 m_2, l_3 m_2\}$ comprises elements that define another orthogonal basis set. One of skill in the art will appreciate that many orthogonal basis sets comprised of linearly independent composite functions $c_{jk}$ may be determined and subsequently used to construct the reflectance function $r(f)$. The basis set chosen may be based upon minimizing errors in the construction of the reflectance function $r(f)$.

Figure 16:
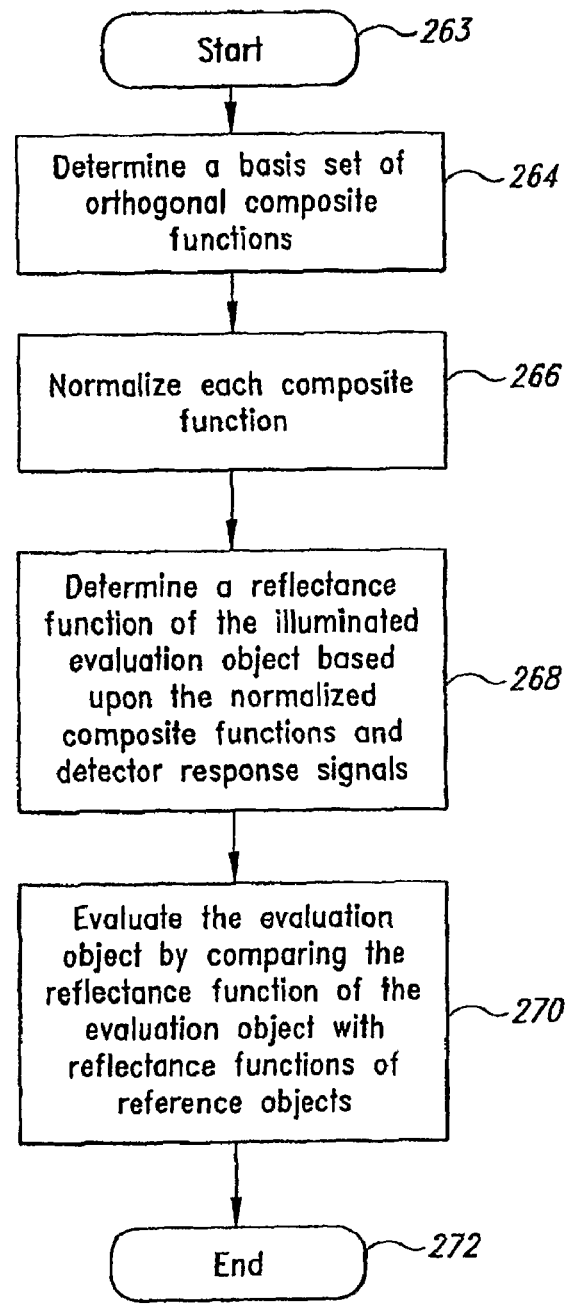
FIG. 16 is a flow chart showing a method of constructing a reflectance function of the evaluation object to evaluate the evaluation object against reference objects, according to one illustrated embodiment.

FIG. 16 is a flow chart showing a method of constructing a reflectance function of the evaluation object 128 to evaluate the evaluation object 128 against reference objects, according to one embodiment.

At 264, a user, the computer system 104 or a manufacturer of the object test device 102, determines an orthogonal basis set $C=\{c_{jk}(f)\}$ of composite functions $c_{jk}(f)$. A composite function $c_{jk}$ of the set C is the product of the spectral emittance function of the $j^{th}$ logical source with the spectral sensitivity of the $k^{th}$ detector element of the sensor 116. The $j^{th}$ logical source is one logical source of the plurality of logical sources generated as the physical sources 118 are driven in a selected sequence by an electromagnetic forcing function. The composite functions are linearly independent if $<c_{jk}, c_{mn}>=0$ when ($j \neq m$, $k \neq n$), ($j=m$, $k \neq n$) or ($j \neq m$, $k=n$). The number of basis functions $c_{jk}$ required to span the composite function frequency space, (i.e., the dimensionality of the frequency space) is equal to the product of the dimensionality of the logical source space and the dimensionality of the detector element space. One of skill in the art will appreciate that there exist many ways to construct an orthogonal basis set $C=\{c_{jk}(f)\}$ of composite functions $c_{jk}(f)$.

At 266, the composite functions are normalized and stored in a memory of the computer system 104 or in the database 106. For example, given a composite function $c_{jk}(f)=l_j(f) m_k(f)$, a normalized composite function $\|c_{jk}(f)\|=\sqrt{(<c_{jk},c_{jk}>)}=\sqrt{(\int c_{jk}(f) c_{jk}(f) df)}$.

At 268, a computing device (e.g., a microprocessor) of the computer system 104 determines the reflectance function of the evaluation object 128 based upon the test response signal produced by the detectors of the sensor 116 and the normalized composite functions $\|c_{jk}(f)\|$ when the physical sources 118 are driven as a number of logical sources to illuminate the evaluation object 128 in a selected sequence. Specifically, the reflectance function $r(f)=\Sigma_{j,k}\{<c_{jk},r>/\|c_{jk}\|\}$, where $<c_{jk},r>=\int l_j(f) m_k(f) r(f) df$. That is, $<c_{jk},r>$ is the test response signal produced by the $k^{th}$ detector element of the sensor 116 when the object evaluation 128 is illuminated by the $j^{th}$ logical source. As an exemplary embodiment, assume that the physical sources 118 comprise three logical sources in which only two of the three logical sources are linearly independent, and the sensor 116 comprises two linearly independent detector elements. Based upon the frequency space occupied by the three logical sources $l_1(f)$, $l_2(f)$, $l_3(f)$ and the two detector elements $m_1(f)$ $m_2(f)$, four linearly independent composite functions $c_{jk}$ may be constructed. In one embodiment, $C=\{c_{jk}\}=\{l_2 m_1, l_3 m_1, l_1 m_2, l_3\ m_2\}$. Other sets comprising four different linearly independent composite functions may also be constructed. A reflectance function of the evaluation object may be constructed based upon a test response signal produced by detector element $m_2$ when the object is illuminated by logical source $l_1$, a signal produced by detector element $m_1$ when the object is illuminated by logical source $l_2$, and test response signals produced by detector elements $m_1$ and $m_2$ when the object is illuminated by logical source $l_3$.

At step 270, the microprocessor evaluates the evaluation object by comparing the reflectance function $r(f)$ determined for the evaluation object 128 to reference reflectance functions stored in the database 106 or in the memory of the computer system 104. In one embodiment, the reference reflectance functions are obtained from the manufacturer(s) of the reference objects or from third party sources, for example. By comparing the reflectance function to the reference reflectance functions, the microprocessor evaluates the evaluation object 128 against the reference objects.

EXAMPLES

Example 1

ID/Passport Verification

A pattern database of passport photos of every U.S. citizen may be searchable within seconds to confirm their identity. For security purposes, the search patterns for the entire database may be changed, for example, in less than thirty minutes or even on demand. This may reduce or eliminate identification document fraud, and also reduces or eliminates the cracking the security code.

The object evaluation system 100 can verify a passport or other identification documentation as follows:

When a passport application is submitted, a photo is included which will be affixed to a validly issued passport. The photo identifies the person submitting the application. Once the issuing authority determines that a passport is to be issued, the issuing authority will generate and store at least one known reference pattern associated with the photo (the reference object in this example), as well as other identity information relating to the identity of the person to whom the passport is issued, such as the person's name, physical characteristics, address, social security number, etc. (other issuance information can also be included if necessary, such as for example the date of issuance). A data file containing the reference pattern and associated identity information is stored in the data structure with a plurality of other reference patterns generated by the issuing authority for other validly issued passports. The issued passport containing the photo is then sent to the person who submitted the application.

At a security checkpoint, for example at an airport terminal, a passport is provided by a traveler for identification purposes. The passport (sampled object) is provided to the object test device 102 of the system 100. A region is selected within the passport photo (the sampled object 128 in this example) for which a spectrum measuring device of the object test device 102 measures the spectral contents, i.e., color information, and outputs information indicative of the same to the computer system 104 or microprocessor operating spatial analysis software.

The spectral content information outputted by the spectrum measuring device is provided as input to the spatial analysis software program, which generates a measured pattern for the sampled passport photo. In some embodiments, the measured pattern may be in the XYZ color space, and/or the measured pattern can be observed from virtually any angle. The measure pattern (or a view key generated therefrom) is compared to the plurality of reference patterns stored in the passport issuing authority's database (or view keys generated therefrom) until a matching reference pattern is found. If a matching reference pattern is not found, then the passport is deemed to be a fraud by the spatial analysis software. If a match is located, identity information associated with the matching reference pattern is analyzed to determine if the identity information for the matching reference pattern substantially corresponds to the identity information associated with the sampled passport photo.

At least a portion of the identity information associated with the sampled passport photo is generally located within the passport, and can be provided to the spatial analysis software for analysis (e.g., by the user entering or scanning the identity information present in the passport), and/or the identity information within the passport can be provided to the human user to perform the comparison. If the identity information associated with the sampled passport photo matches the identity information associated with the matching reference pattern, the passport photo will be deemed an authentic and validly issued passport (i.e., not a forgery) by the spatial analysis software, and the traveler will be permitted to proceed past the security checkpoint.

Further, it should be understood that the materials used to construct the passport (or other identification documentation materials) can be validated against known spectral or color data. The paper and inks can be checked to determine if the passport itself is a forgery, not just the photo or information printed on the document.

Example 2

Document Authentication

The object evaluation system 100 can be used to detect forgeries of a document of value, such as money or bank notes, or other sensitive documents operates as follows:

When a document is validly produced, the producing entity generates and stores at least one reference pattern for the original document (the reference object in this example), as well as other identity information relating to the identity or characteristics of the document, such as the date it was produced, a general title for the document, key terms or monetary value, etc. A data structure containing the reference pattern and identity information associated with the reference pattern is then delivered or made available to an eligible recipient of the original document.

When the recipient is later presented with a document (sampled object 128), the recipient can use the object evaluation system 100 to check the authenticity of the presented document, i.e., to determine whether the presented document is the original document or of the same quality or origin as the original document. It should be understood that if the document is one that is duplicated, such as a dollar bill for example, then only reference patterns for one representative document needs to be used for authentication.

The presented document is provided to a spectrum measuring device of the object test device 102. A region is selected within the presented document (the sampled object 128 in this example) for which the spectrum measuring device measures the spectral content and outputs information indicative of the same to the computing system 104 or microprocessor operating spatial analysis software.

The spectral content information outputted by the spectrum measuring device is provided as input to the spatial analysis software, which generates a measured pattern for the sampled document. The measured pattern (or a view key generated therefrom) is compared to the specific reference pattern previously generated for the original document (or a view key generated therefrom). If the measured pattern does not match the reference pattern, then the presented document is deemed a forgery by the spectral analysis software. If the measured pattern matches the reference pattern, then the presented document is deemed authentic by the spectral analysis software and the recipient can accept the presented document.

For further authentication, the identity information associated with the original document can also be compared to identity information associated with the presented document to determine if they substantially correspond. At least a portion of the identity information associated with the presented document is generally located within the document, and can be provided to the spatial analysis software for analysis (e.g., by the user entering or scanning the identity information present in the document), and/or the identity information within the presented document can be provided to the human user to perform the comparison.

Example 3

Product Monitoring

The object evaluation system 100 can be used for brand protection to verify the authenticity of a product based on the make of its material (e.g., fabric colors) operates as follows:

When a manufacturer mass produces a product, at least one reference pattern for a representative of the product (the reference object in this example) is generated and stored in the reference pattern data structure, as well as identity information associated with the original product, such as the name or style of the product, a serial number, a color description, a size, the manufacturer's name and address, etc.

To determine if the product (sampled object 128) is of the same quality or of the same origin as the original representative product, a distributor or individual consumer can provide the product to be sampled to the object evaluation system 100. A region is selected within the sampled product (the sampled object 128 in this example) for which a spectrum measuring device of the object test device 102 measures the spectral content and outputs information indicative of the same to the computer system 104 or microprocessor operating spatial analysis software.

The spectral content information outputted by the spectrum measuring device is provided as input to the computer system 104 or microprocessor executing the spatial analysis software, which generates a measured pattern for the sampled product 128. The measured pattern (or a view key generated therefrom) is compared to the reference patterns in the data structure (or view keys generated therefrom) until a matching reference pattern is found. If a matching reference pattern is not found, then the sampled product 128 is deemed to be a fraud. If a match is located, then the identity information associated with the matching reference pattern is analyzed to determine if the identity information for the matching reference pattern substantially corresponds to the identity information associated with the sampled product. At least a portion of the identity information associated with the sampled product 128 is generally located on a label or tag on the product, or observable by a human user, and can be provided to the computer system 104 or microprocessor executing the spatial analysis software for analysis (e.g., by the user entering or scanning the identity information present in the label or tag or obtained from observation), and/or the identity information associated with the matching reference pattern can be provided to the human user to perform the comparison. If the identity information associated with the sampled product 128 matches the identity information associated with the matching reference pattern, the sampled product 128 will be deemed authentic and the purchase and/or distribution of the sampled product 128 can proceed. If the measured pattern does not match the reference pattern, then the sampled product 128 is deemed a knock-off or tampered product.

Thus, the object evaluation system 100 can be utilized for brand protection to verify the authenticity of products based on the make of their fabric colors with the pattern of the original product in database, the system 100 can compare a knock off versus the real product in a matter of minutes by scanning any area of the product for which a database pattern exists. In a preferred embodiment, once the fabric has been scanned, a view key is selected to obtain a pattern file. This pattern file will be compared against a pattern from an authentic fabric sample on our database from the same view key point.

Art forgery is another area of product verification that the object evaluation system 100 can be used. That is, spectral data can be taken from one or more regions of a valuable piece of art and this spectral data could be used to authenticate copies or unknown works.

Quality Control of Manufacturing Process

The object evaluation system 100 can be also be used for quality control of manufacturing processes to maintain quality control on practically any manufactured good or the packaging for the good. In this regard, the system 100 would operate as follows:

When a manufacturer mass produces a product, a variety of reference patterns can be taken from the product (reference object) at different locations or areas within the manufacturing process. To determine if the manufacturing process is operating properly, readings can be taken from the products (sampled objects 128) during actual manufacturing and compared to the reference patterns to determine whether the manufacturing process is operating to predetermined quality control standards. Depending upon the results of the comparison, the manufacturing process can be shut down or modified (if the comparison shows unacceptable quality control) or subsequent parts of the manufacturing process can be actuated. For example, if the product (sampled object 128) was a loaf of bread being baked within an oven, then readings could be taken of the loaf of bread and compared with the reference patterns until the comparisons indicate the loaf of bread is ready to be removed from the oven.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other systems for recognizing, identifying, verifying, authenticating, classifying, and/or diagnosing or otherwise evaluating objects such as, but not limited to, manufactured goods and articles; media, for example identity documents, financial instruments, legal documents, other documents and other media; and biological tissue, not necessarily the exemplary networked evaluation system generally described above.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure. The system may, for example include one or more analog to digital converters (ADCs) and/or one or more digital to analog converters (DACs). An ADC may, for example, be used for converting analog photodiode responses into digital data for further analysis and/or transmission. A DAC may, for example, be used for converting digital computer commands into analog LED current levels.

In addition, those skilled in the art will appreciate that the mechanisms of taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to: U.S. provisional patent application Ser. Nos. 60/623,881, filed Nov. 1, 2004; 60/732,163, filed Oct. 31, 2005; 60/820,938, filed Jul. 31, 2006; 60/834,662, filed Jul. 31, 2006; and 60/834,589, filed Jul. 31, 2006; 60/871,639, filed Dec. 22, 2006; 60/883,312, filed Jan. 3, 2007; and 60/890,446, filed Feb. 16, 2007; and U.S. nonprovisional patent application Ser. No. 11/264,626, filed Nov. 1, 2005, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system for evaluating objects, the system comprising:
   at least one physical source operable to emit electromagnetic energy;

driver electronics drivingly coupled to the at least one physical source, the driver electronics configured to drive the at least one physical source with an electromagnetic forcing function as a number of logical sources, at least some of the logical sources having a different emission spectra than other of the logical sources, the number of logical sources greater than a number of physical sources of the at least one physical source; and a sensor configured to receive an electromagnetic response from at least a portion of at least one evaluation object being evaluated, the evaluation object illuminated by one or more of the at least one physical source operated as one of the logical sources and convert the electromagnetic response to a response signal indicative of the electromagnetic response of the at least one evaluation object.

2. The system of claim 1, further comprising a computing device configured to receive the response signal and compare the received response signal with a plurality of reference signals to evaluate the at least one evaluation object, the plurality of reference signals indicative of electromagnetic responses to illumination of a reference object with electromagnetic energy.

3. The system of claim 2, further comprising:
a database configured to store the plurality of reference signals.

4. The system of claim 3 wherein the database is further configured to store source normalization values corresponding to the at least one physical source.

5. The system of claim 4 wherein the computing device is further configured to:
normalize the response signal based upon the stored source normalization values; and
compare the normalized response signal to at least one of the stored plurality of reference signals corresponding to the reference objects to evaluate the evaluation object.

6. The system of claim 4, wherein the normalization values depend upon an ambient operating temperature of at least the at least one physical source.

7. The system of claim 1, further comprising:
a focusing device, wherein the sensor is a detector array, each detector of the detector array configured to receive via the focusing device, an electromagnetic response from a respective region of the at least one evaluation object when illuminated by electromagnetic energy and convert the electromagnetic response to a signal.

8. The system of claim 7 wherein each detector of the detector array is further configured to be at least partially responsive to electromagnetic responses having spectral components between 200-900 nanometers.

9. The system of claim 7 wherein the detector array is a charge coupled device.

10. The system of claim 1 wherein the system comprises a plurality of physical sources and the driver electronics are further configured to drive at least two of the plurality of physical sources in a selected sequence.

11. The system of claim 1 wherein the system comprises a plurality of physical sources and the driver electronics are further configured to drive at least two of the plurality of physical sources such that the at least two physical sources are driven for time periods that overlap.

12. The system of claim 1 wherein the electromagnetic forcing function is a varying current.

13. The system of claim 12 wherein a magnitude of the current is indicative of a logical source associated with a physical source of the at least one physical source.

14. The system of claim 12 wherein the current is a sawtooth current.

15. The system of claim 1, further comprising:
a source mount assembly for mounting the at least one physical source, the source mount assembly configured to move the mounted at least one physical source with respect to the at least one evaluation object.

16. The system of claim 15 wherein the source mount assembly is further configured to move the mounted at least one physical source with respect to the sensor.

17. The system of claim 15 wherein the source mount assembly is further configured to rotate the mounted at least one physical source about at least one axis.

18. The system of claim 17 wherein the source mount assembly includes a surface for mounting the at least one physical source, the source mount assembly further configured to rotate the mounted at least one physical source about a first axis at a variable angular frequency, the first axis perpendicular to the surface.

19. The system of claim 18 wherein the source mount assembly is further configured to rotate the mounted at least one physical source through a variable angle about a second axis, the second axis perpendicular to the first axis.

20. The system of claim 1 wherein the at least one physical source includes at least one light emitting diode.

21. The system of claim 1 wherein the at least one physical source includes at least one tunable laser.

22. The system of claim 1 wherein the at least one physical source emits electromagnetic energy including wavelengths between 200-900 nanometers.

23. The system of claim 1 wherein at least one of the different emission spectra overlaps with at least one other of the different emission spectra.

24. The system of claim 1 wherein the system comprises a plurality of physical sources configured in a circular pattern.

25. The system of claim 24 wherein a center of the sensor is positioned along an axis, the axis passing through a center of the circular pattern and perpendicular to a plane in which the circular pattern lies.

26. The system of claim 1 wherein the sensor is further configured to be responsive to electromagnetic responses having spectral components between 200-900 nanometers.

27. The system of claim 1 wherein the sensor is at least one of a photodiode, a photomultiplier, or a charge coupled device.

28. The system of claim 2 wherein the computing device is further configured to perform a root mean square analysis in comparing the received response signal with the plurality of reference signals.

29. The system of claim 1, further comprising:
an electromagnetic energy directional assembly configured to modify an angle of incidence of electromagnetic energy emitted by one or more physical sources of the at least one physical source with a surface of the at least one evaluation object.

30. The system of claim 29 wherein the electromagnetic energy directional assembly is a lens positioned between the at least one physical source and the at least one evaluation object, the lens having a circumferential portion that refracts the electromagnetic energy emitted by the one or more physical sources of the at least one physical source.

31. The system of claim 30 wherein the circumferential portion has a variable effective index of refraction.

32. The system of claim 29 wherein the electromagnetic energy directional assembly is a mirror positioned between the at least one physical source and the at least one evaluation object, the mirror having a circumferential portion that reflects the electromagnetic energy emitted by the one or more physical sources of the at least one physical source.

33. The system of claim 32 wherein the circumferential portion has a variable angle of incidence with respect to the electromagnetic energy emitted by the one or more physical sources of the at least one physical source and reflected by the circumferential portion of the mirror.

34. The system of claim 1, further comprising a computing device configured to receive the response signal, determine a reflectance function for the at least one evaluation object based upon the received response signal and compare the reflectance function with a plurality of reference reflectance functions to evaluate the at least one evaluation object.

35. The system of claim 7, further comprising a computing device configured to receive the signal from each detector of the detector array and determine a reflectance function based upon a linearly independent set of composite functions.

36. The system of claim 35, wherein a composite function of the linearly independent set of composite functions is a product of a spectral emittance function of a logical source of the number of logical sources and a detector response function of a detector of the detector array.

37. A system for evaluating subject objects, the system comprising:
    a plurality of physical sources operable to emit electromagnetic energy; and
    driver electronics drivingly coupled to the plurality of physical sources, the driver electronics configured to drive the plurality of physical sources with an electromagnetic forcing function as a number of logical sources, at least some of the logical sources having a different emission spectra than other of the logical sources, the number of logical sources greater than the plurality of physical sources, and the plurality of physical sources further operable to receive an electromagnetic response from at least a portion of at least one evaluation object illuminated by at least one physical source of the plurality of physical sources driven as at least two of the logical sources and convert the received electromagnetic response to a response signal.

38. The system of claim 37 wherein at least one of the physical sources emits electromagnetic energy when driven during a first time, and produces the response signal in response to the received electromagnetic response when not driven at a second time.

39. The system of claim 38 wherein the physical sources are driven in a selected sequence.

40. The system of claim 37 wherein a first set of physical sources of the plurality of physical sources are driven by the driver electronics to illuminate the evaluation object while the first set of physical sources convert the received electromagnetic response to the response signal.

41. The system of claim 40 wherein physical sources of the first set of physical sources are driven in a selected sequence.

42. A method of evaluating an evaluation object with respect to at least one reference object, the method comprising:
    driving at least one physical source of a plurality of physical sources with an electromagnetic forcing function as a plurality of logical sources for each of at least some of the physical sources being driven;
    receiving an electromagnetic response from at least a portion of an illuminated region of the evaluation object; and
converting the electromagnetic response to a response signal indicative of the response of the illuminated portion of the evaluation object.

43. The method of claim 42, further comprising comparing the response signal corresponding to the evaluation object with a stored reference signal indicative of a response by the at least one reference object to illumination by electromagnetic energy.

44. The method of claim 43, further comprising:
    determining a plurality of reference signals indicative of electromagnetic responses to illumination of the at least one reference object, each of the reference signals of the plurality of reference signals based upon a broadband spectral response of the at least one reference object, a plurality of emission spectra corresponding to the plurality of logical sources for each of at least some of the physical sources being driven and a spectral sensitivity of at least one sensor; and
    storing the plurality of reference signals.

45. The method of claim 44 wherein each emission spectrum of the plurality of emission spectra associated with each logical source of the plurality of logical sources corresponds to a state of the electromagnetic forcing function.

46. The method of claim 43 wherein comparing further comprises determining root-mean-square values to evaluate the evaluation object.

47. The method of claim 42 wherein the plurality of physical sources are configured to emit electromagnetic energy having wavelengths between 200-900 nanometers.

48. The method of claim 42 wherein driving at least one physical source of a plurality of physical sources with an electromagnetic forcing function includes driving the at least one physical source with a saw-tooth current.

49. The method of claim 44 wherein the at least one sensor is responsive to the electromagnetic responses having spectral components between 200-900 nanometers.

50. The method of claim 42 wherein at least some of the physical sources of the plurality of physical sources have different emission spectra than other of the physical sources.

51. The method of claim 42, wherein converting further comprises converting the electromagnetic response to a plurality of response signals, each response signal of the plurality of response signals corresponding to detection of the electromagnetic response by a detector of a plurality of detectors.

52. The method of claim 51, further comprising determining a reflectance function of the evaluation object based upon the plurality of response signals and a linearly independent set of composite functions.

53. The method of claim 52, wherein a composite function of the linearly independent set of composite functions is a product of a spectral emittance function of a logical source of the plurality of logical sources and a detector response function of one detector of the plurality of detectors.

54. An electronic-readable medium having embodied thereon a program, the program being executable by a machine to perform a method for evaluating an evaluation object with respect to at least one reference object, the method comprising:
    driving at least one physical source of a plurality of physical sources with an electromagnetic forcing function as a plurality of logical sources for each of at least some of the physical sources being driven wherein each of the logical sources is characterized by a respective band of emission, and at least two of the logical sources of each of the physical sources have different bands of emission from one another;
    receiving an electromagnetic test response from at least a portion of an illuminated region of the evaluation object;

converting the electromagnetic response to a test response signal representative of the test response of the illuminated portion of the evaluation object; and comparing the test response signal corresponding to the evaluation object with a stored reference response signal indicative of a response by the at least one reference object to illumination by electromagnetic energy.

55. A system for evaluating subject objects, the system comprising:

a plurality of physical sources operable to emit electromagnetic energy, at least some of the physical sources of the plurality of physical sources having different emission spectra than other of the physical sources;

driver electronics drivingly coupled to the plurality of physical sources, the driver electronics configured to drive at least two of the physical sources of the plurality of physical sources in a plurality of selected sequences; and a sensor configured to receive an electromagnetic response from at least a portion of at least one evaluation object illuminated by at least one of the physical sources of the plurality of physical sources and convert the electromagnetic response to a response signal.

56. The system of claim 55 wherein the driver electronics is further configured to drive two or more of the at least two physical sources for time periods that at least partially overlap.

* * * * *